US009283342B1

(12) United States Patent
Gardner

(10) Patent No.: US 9,283,342 B1
(45) Date of Patent: Mar. 15, 2016

(54) ENDOTRACHEAL TUBE INSERTION DEVICE

(71) Applicant: Glenn P. Gardner, Oak Brook, IL (US)

(72) Inventor: Glenn P. Gardner, Oak Brook, IL (US)

( * ) Notice: Subject to any disclaimer, the term of this patent is extended or adjusted under 35 U.S.C. 154(b) by 0 days.

(21) Appl. No.: 14/827,508

(22) Filed: Aug. 17, 2015

Related U.S. Application Data

(60) Provisional application No. 62/128,319, filed on Mar. 4, 2015.

(51) Int. Cl.
*A61M 16/04* (2006.01)
*A61B 1/267* (2006.01)

(52) U.S. Cl.
CPC ............ *A61M 16/0488* (2013.01); *A61B 1/267* (2013.01); *A61M 16/0447* (2014.02)

(58) Field of Classification Search
CPC ....................................................... A61B 1/267
See application file for complete search history.

(56) References Cited

U.S. PATENT DOCUMENTS

| | | | |
|---|---|---|---|
| 5,184,603 A | 2/1993 | Stone | |
| 5,443,058 A | 8/1995 | Ough | |
| 5,489,256 A | 2/1996 | Adair | |
| 5,551,946 A * | 9/1996 | Bullard | A61B 1/2676 600/114 |
| 5,607,386 A | 3/1997 | Flam | |
| 5,645,519 A | 7/1997 | Lee et al. | |
| 5,665,052 A | 9/1997 | Bullard | |
| 6,146,402 A | 11/2000 | Munoz | |
| 6,585,642 B2 | 7/2003 | Christopher | |
| 6,878,106 B1 | 4/2005 | Herrmann | |
| 6,929,600 B2 | 8/2005 | Hill | |
| 7,563,227 B2 | 7/2009 | Gardner | |
| 7,706,861 B2 | 4/2010 | Windheuser et al. | |
| 7,771,396 B2 | 8/2010 | Stefanchik et al. | |
| 7,815,565 B2 | 10/2010 | Stefanchik et al. | |
| 8,667,966 B2 | 3/2014 | Koike | |
| 8,777,840 B2 | 7/2014 | Belafsky | |
| 8,845,525 B2 | 9/2014 | McGrath et al. | |
| 2004/0210114 A1 | 10/2004 | Simon | |
| 2006/0258903 A1 | 11/2006 | Stefanchik et al. | |
| 2006/0258904 A1 | 11/2006 | Stefanchik et al. | |
| 2007/0066869 A1 | 3/2007 | Hoffman | |
| 2007/0225554 A1 | 9/2007 | Maseda et al. | |
| 2013/0023729 A1 | 1/2013 | Vazales et al. | |
| 2013/0030249 A1 | 1/2013 | Vazales et al. | |

OTHER PUBLICATIONS

Ketaminh, "King Vision Bougie Supreme—refining a novel hybrid intubation technique", Pharm: Prehospital and Retrieval Medicine, 2012.

* cited by examiner

*Primary Examiner* — Andrew Yang
(74) *Attorney, Agent, or Firm* — MacMillan, Sobanski & Todd, LLC

(57) ABSTRACT

An endotracheal tube insertion device includes an insertion member, an optical assembly movably mounted to the insertion member, and an intubation assembly. The intubation assembly includes an intubation assembly body and has a guide system formed thereon. The guide system is configured for releasable attachment to the optical assembly. An endotracheal tube carried by the intubation assembly body.

27 Claims, 20 Drawing Sheets

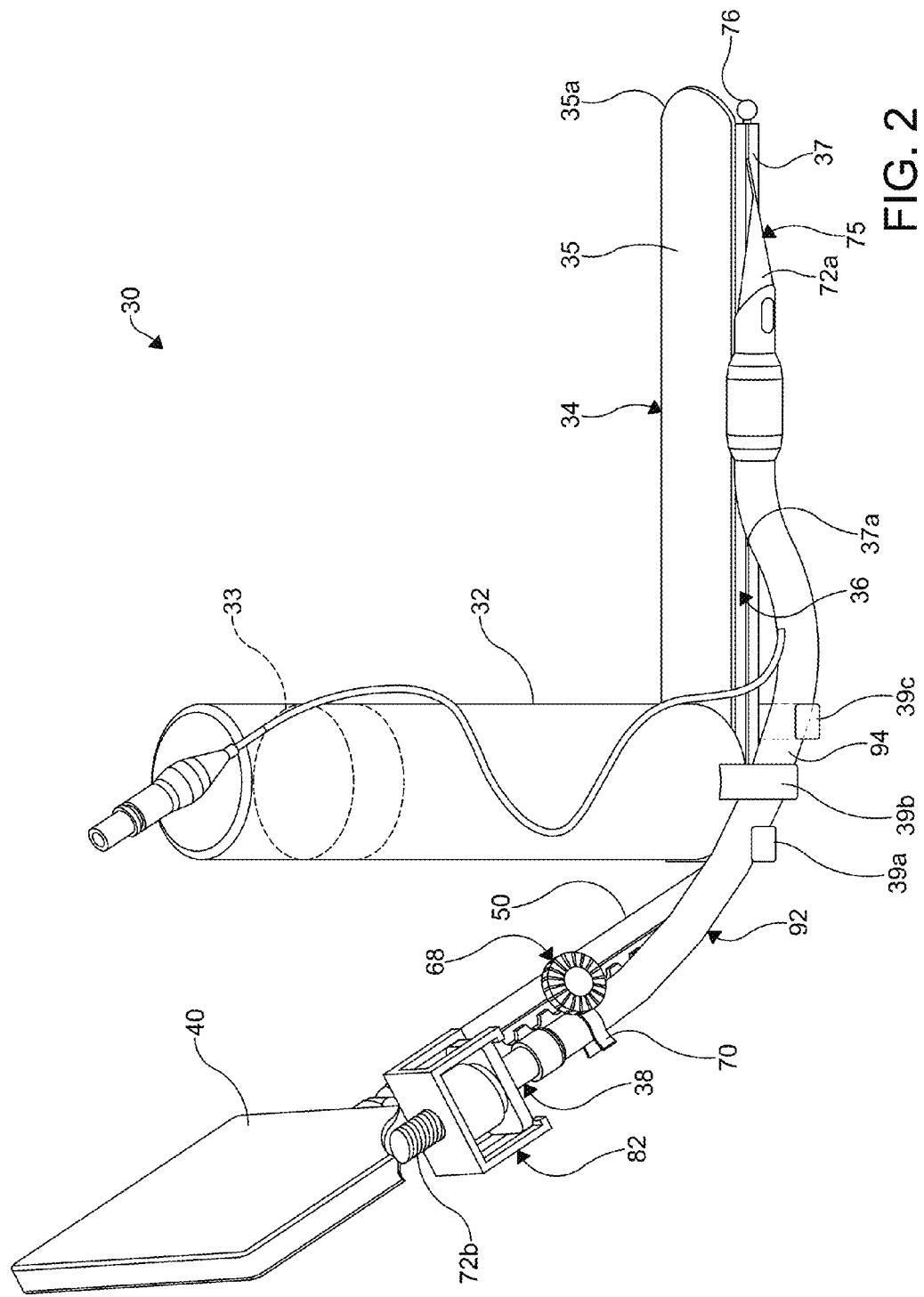

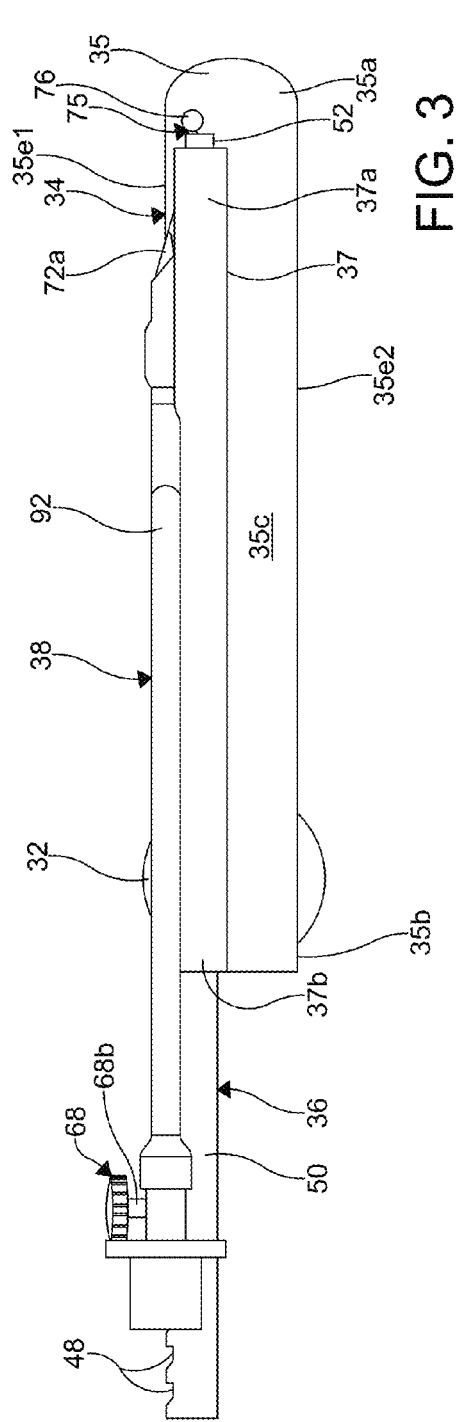
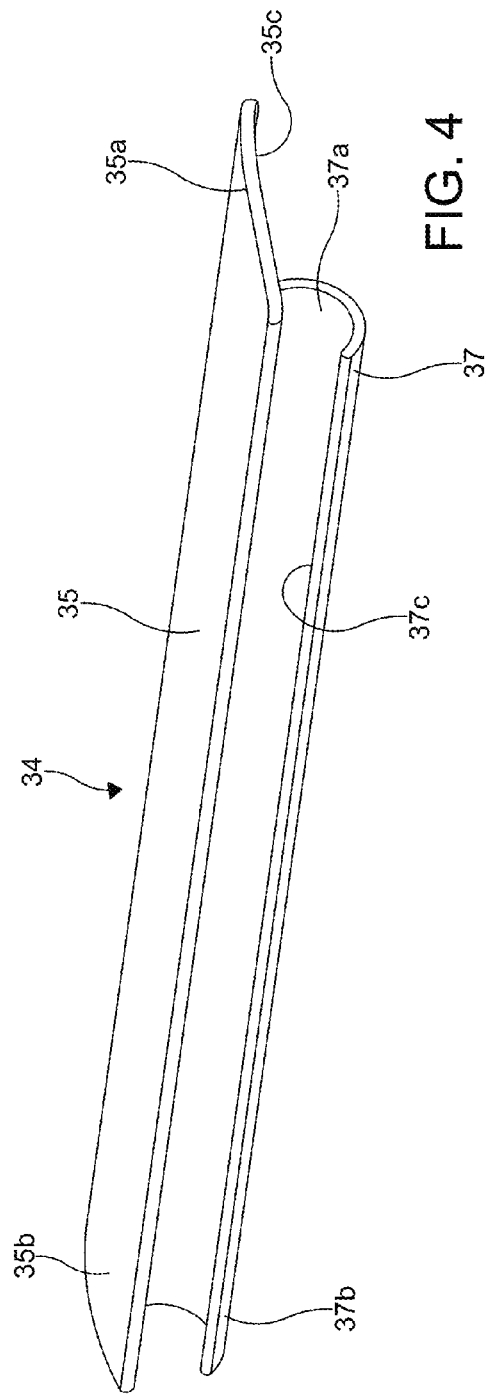

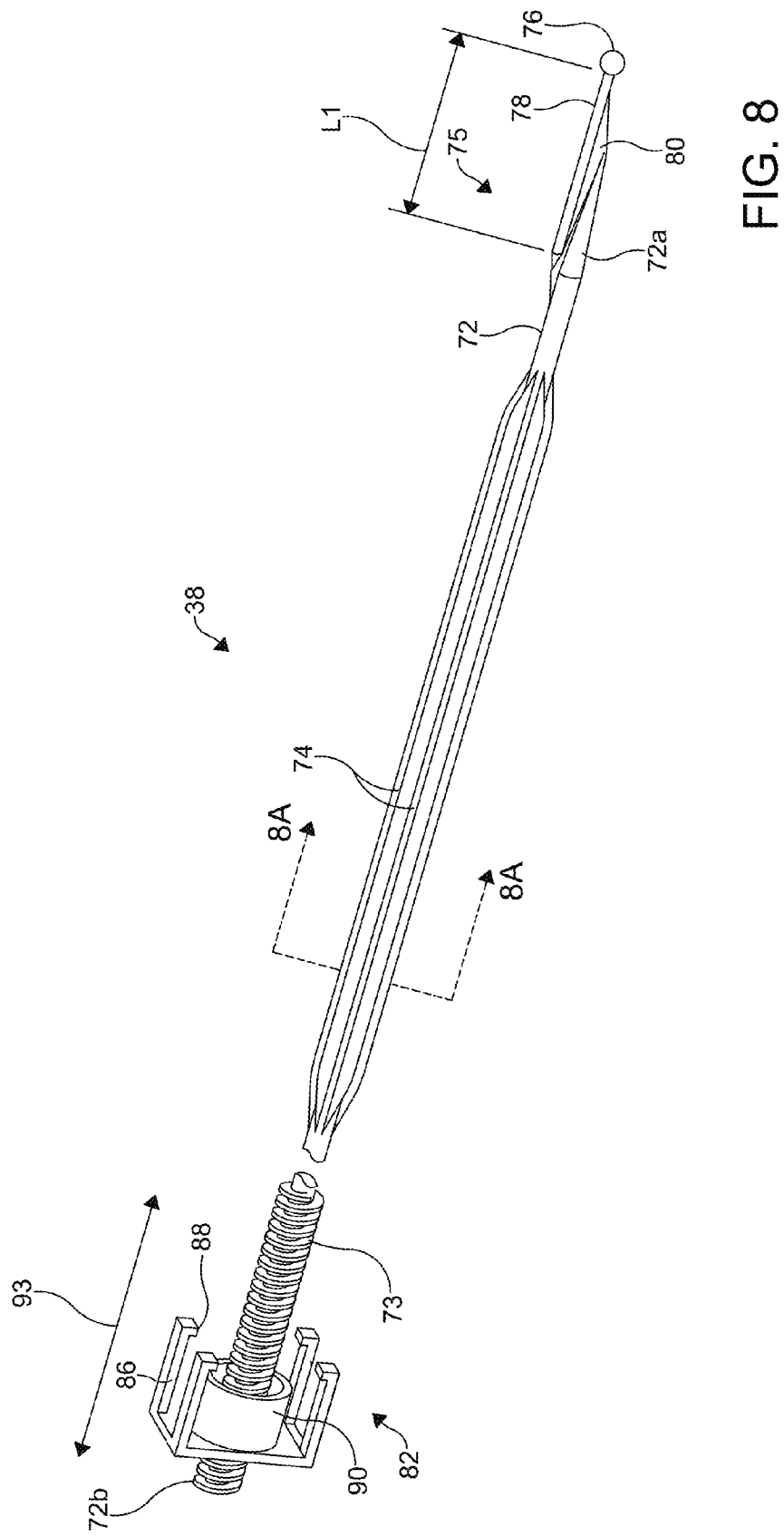

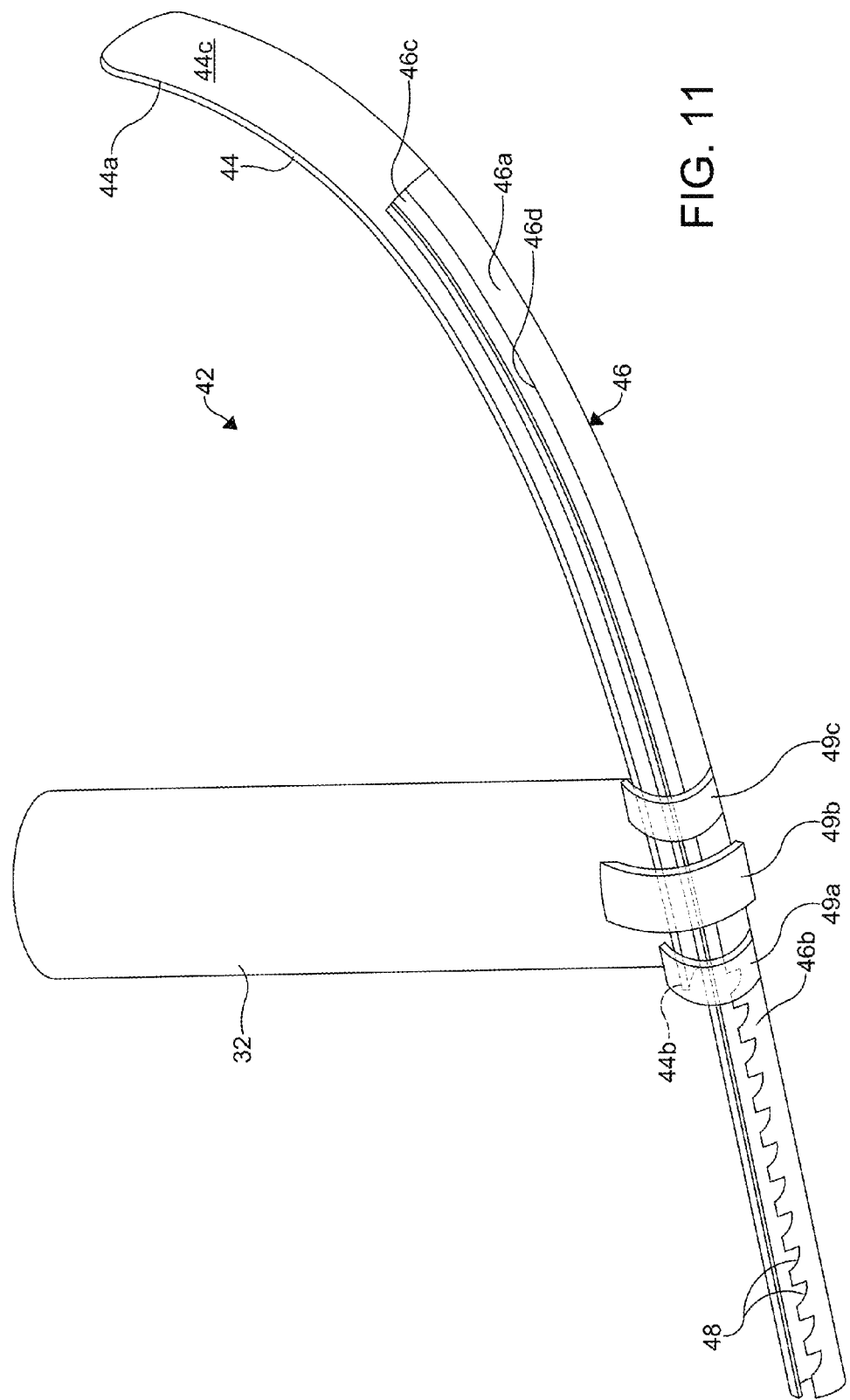

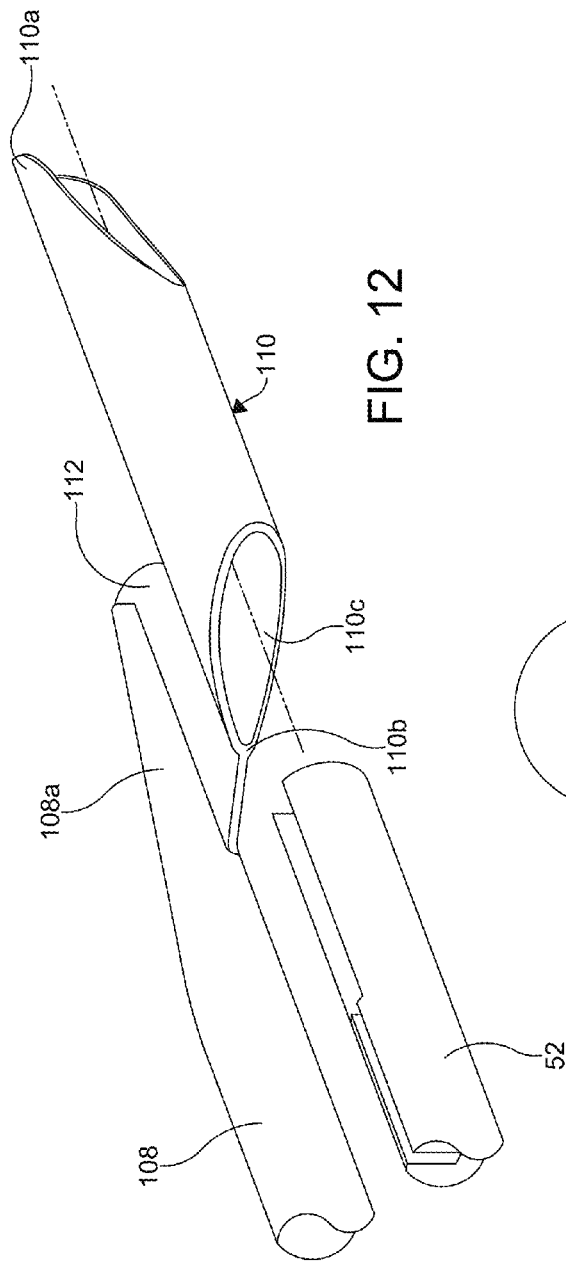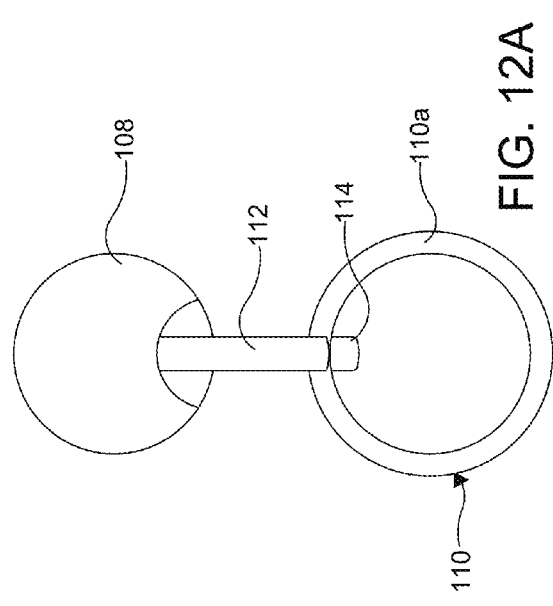

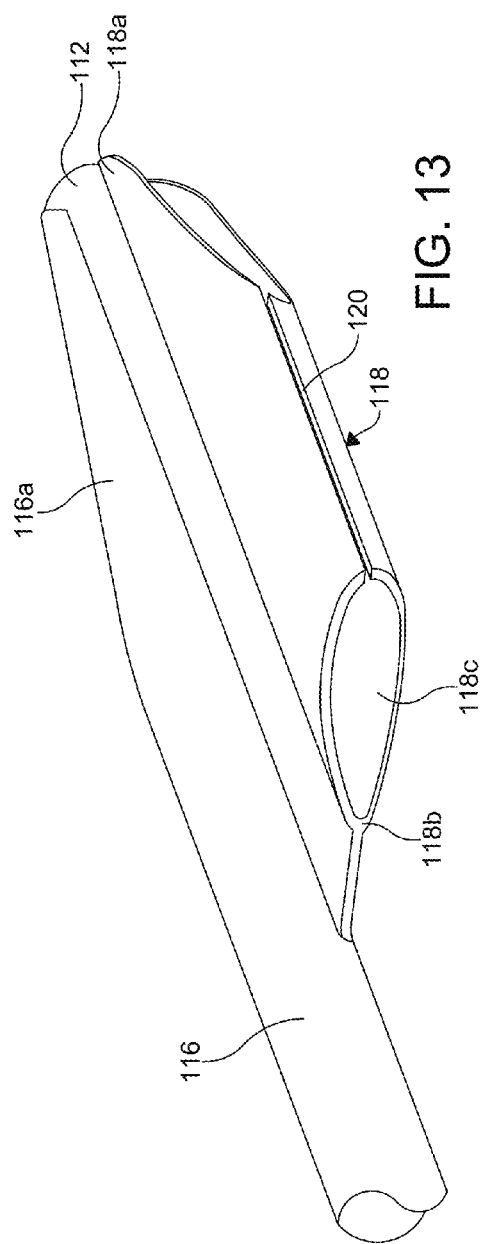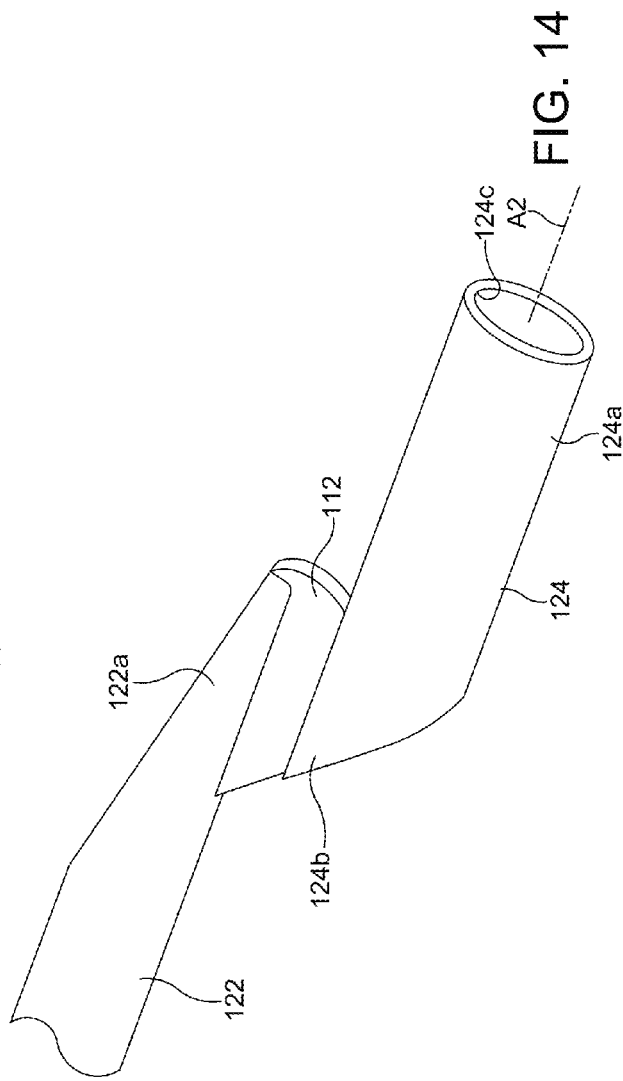

ENDOTRACHEAL TUBE INSERTION DEVICE

CROSS REFERENCE TO RELATED APPLICATIONS

This application claims the benefit of U.S. Provisional Application No. 62/128,319 filed Mar. 4, 2015, the disclosure of which is incorporated herein by reference.

BACKGROUND OF THE INVENTION

This invention relates in general to a device for introducing an intubation device, such as an endotracheal tube, into a patient. In particular, this invention relates to an improved endotracheal tube insertion device that allows the user to simultaneously open the airway, view a patient's airway, accurately position an intubation device within the airway, and transmit a video image of the patient's airway to the operator and/or a medical professional located remotely from the patient.

Tracheal intubation typically includes placing a flexible plastic tube into the trachea or windpipe to maintain an open airway or to serve as a conduit through which to administer certain drugs. Tracheal intubation is frequently performed in critically injured, ill, or anesthetized patients to facilitate ventilation of the lungs, including mechanical ventilation, and to prevent the possibility of asphyxiation or airway obstruction. The most widely used method is orotracheal intubation, in which an endotracheal tube is passed through the mouth and vocal cords into the trachea.

Intubation is normally facilitated by using a conventional laryngoscope, a video laryngoscope, a flexible fiber-optic bronchoscope, or a flexible videoscope to identify the glottis and intubate the trachea of a patient, although other devices and techniques may be used. After the trachea has been intubated, a balloon cuff is typically inflated just above the far end of the tube to help secure the endotracheal tube in place, to prevent leakage of respiratory gases, and to protect the tracheobronchial tree from receiving undesirable material such as stomach acid. The endotracheal tube is then secured to the patient's face or neck and connected to a breathing device, such as a mechanical ventilator. Once there is no longer a need for ventilatory assistance and/or protection of the airway, the endotracheal tube is removed.

Many conventional tracheal intubations involve the use of a viewing instrument. For example, a conventional laryngoscope may consist of a handle containing batteries that power a light, and a set of interchangeable rigid blades, which are either straight or curved. This device is designed to allow the laryngoscopist to directly view the larynx.

Video laryngoscopes, flexible fiber-optic bronchoscopes, and flexible videoscopes have also become increasingly available. Video laryngoscopes are specialized rigid blade laryngoscopes that use a digital video camera sensor to allow the operator to view the glottis and larynx on a video monitor. In contrast to the conventional laryngoscope, a video laryngoscope allows the laryngoscopist to indirectly view the larynx. This provides a significant advantage in situations where the operator needs to see around an acute bend in order to see the glottis, and with otherwise difficult intubation procedures. Flexible videoscopes and fiber-optic bronchoscopes are not rigid instruments, and provide an even greater opportunity for visualizing the vocal cords due to their ability to fully manipulate the angle and position of the camera sensor and optics.

Successful endotracheal intubation requires adequate atraumatic laryngeal retraction, visualization of the vocal cords, positioning of the endotracheal tube, and a clear passage of the endotracheal tube into the trachea. Failure to adequately place the endotracheal tube within a few minutes often leads to permanent patient disability and even death. Currently available intubation instruments frequently lack the capability to meet one or more of these requirements.

Visualization of the vocal cords requires retraction of the tongue and laryngeal structures such as the epiglottis. Large tongues, excessive oropharyngeal soft tissue, stiff and immobile necks, and unique patient anatomy can make vocal cord visualization challenging. The ability to retract and physically align the oropharyngeal and laryngeal structures properly for direct or camera assisted viewing with a rigid blade may be difficult or impossible. Flexible videoscopes and fiber-optic bronchoscopes are not able to retract the tongue and laryngeal structures.

Direct rigid blade laryngoscopy allows for adequate retraction of laryngeal structures, but is often limited in providing vocal cord visualization in certain patient populations (e.g., thick, stiff, and/or immobile necks) and can be traumatic when trying to improve the view by manipulating the rigid blade between the teeth and stretching the laryngeal tissues.

Indirect rigid blade videoscopes improve the field of vision over direct rigid blades, but because the camera tip is permanently mounted on a singular site on the rigid blade, practitioners must still use rigid blade manipulation to further improve or achieve visualization of the vocal cords, often resulting in trauma as occurs with direct oral laryngoscopy. Despite manipulating the rigid blade videoscope and its fixed camera, the angle, curvature, and depth is often limited and visualization of the vocal cords may not be achieved.

Flexible videoscopes and fiber optic bronchoscopes provide for multiple angles and depths of view. Unfortunately, they do not provide a means to retract the tongue and laryngeal tissues that allow for visualization of the vocal cords. Instead, one must use a separate airway to retract the tongue and/or a second practitioner to manually retract or displace the tongue or the mandible. Although it is known to use flexible fiber-optic bronchoscopes or flexible videoscopes during intubation when the patient is under general anesthesia, the use of such devices has the disadvantage of typically requiring two skilled individuals to intubate the patient. It is difficult to manipulate soft tissue in the larynx with flexible fiber-optic bronchoscopes and flexible videoscopes, and despite these maneuvers for visualization, the passage, and the delivery of the endotracheal tube into the trachea is often inhibited by the laryngeal structures.

Despite proper tissue retraction and visualization of the vocal cords with currently available instruments such as a direct laryngoscope, indirect video laryngoscope, or a flexible videoscope, the delivery, placement, and passage of the endotracheal tube is often challenging. Stiff, rigid, and potentially traumatic stylets are frequently shaped and placed within the endotracheal tube, to give more control and guidance to the endotracheal tube tip in the direction of the visualized vocal cords. However, once the rigid stylet has been manually shaped, the user must work with that specific curvature and shape. If the curvature and shape is not satisfactory, the user must stop the laryngoscopy, remove all of the equipment, manually reshape the stylet, and start the procedure over from the beginning.

It is often the case with flexible videoscopes, flexible fiber-optic bronchoscopes, and rigid direct or indirect laryngoscopes, that visualization of the vocal cords may be achieved wherein placement of the endotracheal tube tip is at the vocal cords, or the flexible scope is within the trachea, but the passage of the endotracheal tube tip through the larynx between the vocal cords and into the trachea is obstructed. The leading edge of the endotracheal tube tip often collides with laryngeal structures, such as the arytenoids or the anterior wall of the trachea, preventing smooth passage of the endotracheal tube into the trachea.

In urgent and emergency situations, especially in locations remote from a hospital, the use of flexible video laryngoscopy or fiber-optic bronchoscopy may be limited, and personnel experienced in performing direct or indirect laryngoscopy are not always immediately available in settings that require emergency tracheal intubation.

It would therefore be desirable to provide an improved structure for a device for introducing an endotracheal tube into a patient, wherein such an improved device allows the user to simultaneously open the airway, view a patient's airway, accurately position an endotracheal tube or other intubation device within the airway, and if desired, transmit a video image of the patient's airway to the operator and/or a medical professional located remotely from the patient.

SUMMARY OF THE INVENTION

This invention relates to an improved structure for a device for introducing an endotracheal tube into a patient. The improved device is configured to allow the user to simultaneously open the airway, view a patient's airway, accurately position an endotracheal tube or other intubation device within the airway, and transmit a video image of the patient's airway to the operator and/or a medical professional located remotely from the patient.

In one embodiment, the improved endotracheal tube insertion device includes an insertion member, an optical assembly movably mounted to the insertion member, and an intubation assembly. The intubation assembly includes an intubation assembly body and has a guide system formed thereon. The guide system is configured for releasable attachment to the optical assembly. An endotracheal tube carried by the intubation assembly body.

In a second embodiment, the endotracheal tube insertion device includes a supraglottic member having an optical assembly movably mounted thereto, and an endotracheal tube carried by the optical assembly.

In a third embodiment, an intubation assembly for use in an endotracheal tube insertion device includes a rod having an elongated body having a first end and a second end. A guide system is formed at the first end of the rod, and a connecting member is mounted to the second end of the rod, wherein the first end of the rod is a distal end of the rod, and wherein the distal end of the rod is tapered.

In a fourth embodiment, the endotracheal tube insertion device includes a supraglottic member and an optical assembly movably mounted thereto. An intubation assembly includes an intubation assembly rod having a guide system formed on the intubation assembly rod. The guide system is configured for releasable attachment to the optical assembly.

Various aspects of this invention will become apparent to those skilled in the art from the following detailed description of the preferred embodiment, when read in light of the accompanying drawings.

BRIEF DESCRIPTION OF THE DRAWINGS

FIG. 2 is a perspective view of a first embodiment of an improved endotracheal tube insertion device in accordance with this invention.

FIG. 3 is a bottom plan view of a portion of the improved endotracheal tube insertion device illustrated in FIG. 2.

FIG. 4 is a perspective view of the blade assembly illustrated in FIGS. 2 and 3.

FIG. 8 is an exploded perspective view of the intubation assembly rod illustrated in FIGS. 2 and 3.

FIG. 11 is a perspective view of a second embodiment of the blade assembly illustrated in FIG. 4.

FIG. 12 is a perspective view of a third embodiment of the intubation assembly rod illustrated in FIG. 8.

FIG. 12A is an end view of the third embodiment of the intubation assembly rod illustrated in FIG. 12.

FIG. 13 is a perspective view of a fourth embodiment of the intubation assembly rod illustrated in FIG. 8.

FIG. 14 is a perspective view of a fifth embodiment of the intubation assembly rod illustrated in FIG. 8.

DETAILED DESCRIPTION OF THE INVENTION

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Figure 1:
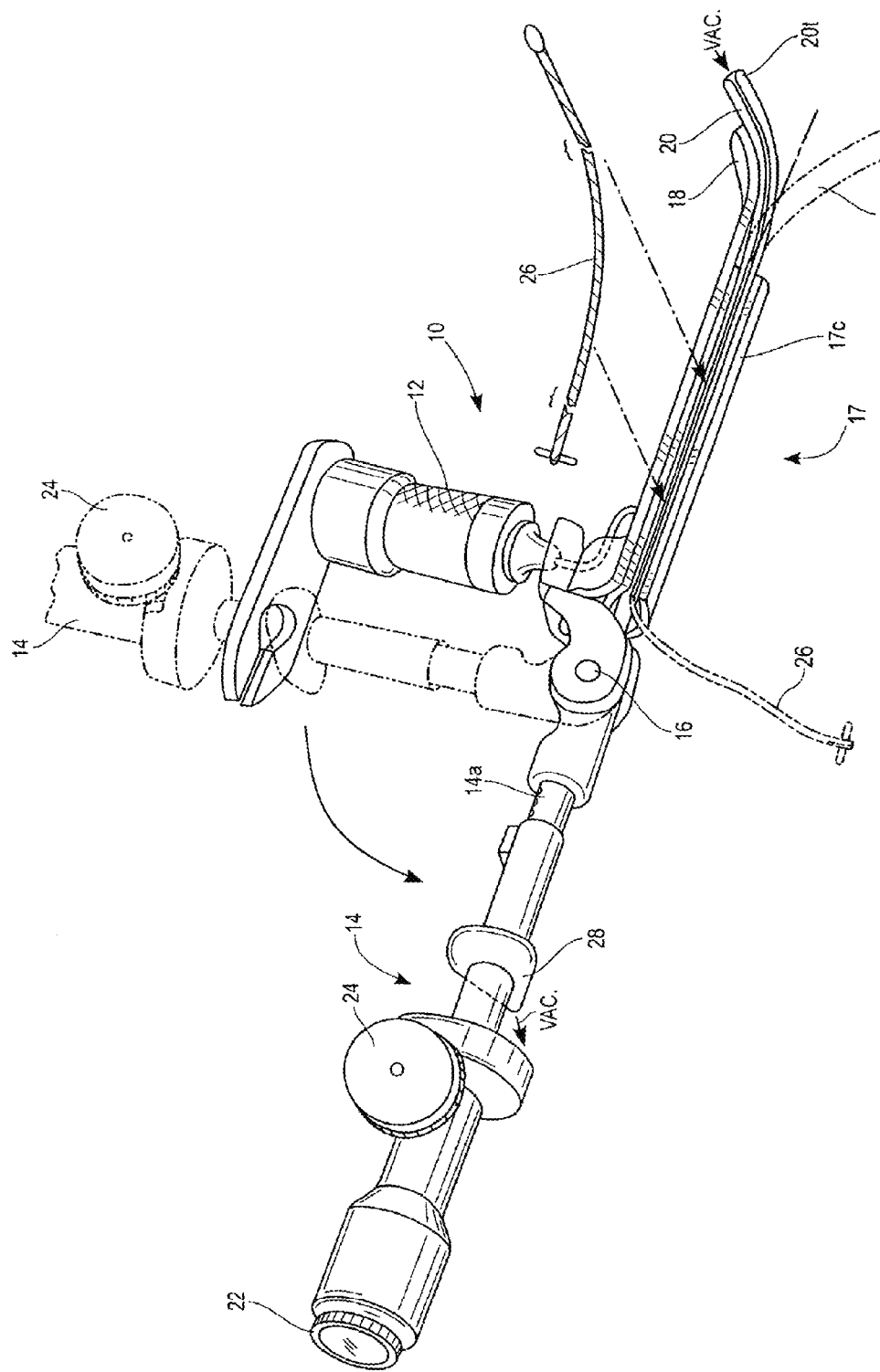
FIG. 1 is a perspective view of a known laryngoscope.

Referring now to the drawings, an embodiment of a known laryngoscope is indicated generally at 10 in FIG. 1. The illustrated laryngoscope 10 is described in detail in U.S. Pat. No. 7,563,227 to Gardner, the disclosure of which in incorporated herein in its entirety.

As shown in FIG. 1, the laryngoscope 10 includes a handle 12 and a viewing member 14. The viewing member 14 is made so that it can telescope between a first extended position and a second contracted position. A telescoping portion 14a is attached at a hinge 16 to a blade portion 17 having a blade 18. The viewing member 14 is configured such that it can be moved to first folded position parallel to the handle 12, as illustrated by phantom lines in FIG. 1.

The laryngoscope 10 also includes a flexible tubular member 20 adjacent to the blade 18. An eyepiece 22 and a ratcheting member 24 are operationally attached to the flexible tubular member 20. A generally C-shaped rigid channel 17c is provided on an underside of the blade 18 and is configured to hold the flexible tubular member 20 and to act as a guide for the flexible tubular member 20 when it is advanced. The flexible tube member 20 is configured such that it can be advanced forward (to the right when viewing FIG. 1) through the channel 17c so that a tip 20t of the flexible tube member 20 is distal of the end of the blade 18, to provide a better view of the patient's anatomy.

The flexible tube member 20 includes a plurality of longitudinally extending channels (not shown in FIG. 1). The channels may be configured for a variety of uses, including as a suction tube, or within which implements such as a fiber optic scope, illumination means, or a guidewire 26 may be mounted. The guidewire 26 is configured to be inserted through a conventional endotracheal tube, not shown in FIG. 1. The suction tube may be attached to a vacuum port 28, which may be further connected to a source of suction (not shown) external to the laryngoscope 10.

FIGS. 2 through 15 illustrate portions of an improved endotracheal tube insertion device, indicated generally at 30. The improved endotracheal tube insertion device 30 is an improved device for introducing an intubation device, such as a conventional endotracheal tube 92, shown in FIG. 9, into a patient. The improved endotracheal tube insertion device 30 is configured to allow the user to simultaneously open the airway, view a patient's airway, accurately position the endotracheal tube 92 within the airway, and transmit a video image of the patient's airway.

The improved endotracheal tube insertion device 30 includes a handle 32 attached to a blade assembly 34, an optical assembly 36, and a guided introducer intubation assembly 38. In the embodiment illustrated in FIGS. 2 and 3, the handle 32 is configured to be gripped by the hand of the user of the endotracheal tube insertion device 30.

A video monitor 40 is attached to a proximal end of the optical assembly 36 and is operationally connected to a video imaging device 60, shown in FIG. 7 and described below, within the optical assembly 36. In the illustrated embodiment, the video monitor 40 is mounted to a flexible member 52, described in detail below, such that it is movable or adjustable to any desired angle for ease in viewing. The video monitor 40 may also be releasably attached to the optical assembly 36 for remote viewing at a distance from the patient. Further, one or more additional video monitors 40 (not shown) may be positioned remotely from the endotracheal tube insertion device 30 and connected thereto by a wired or a wireless connection. Alternatively, the video monitor 40 may also be attached, including releasably attached, to the handle 32. In the illustrated embodiment, the video monitor has a substantially rectangular shape. Alternatively, the video monitor 40 may have any desired shape and size.

The handle 32 may also include a processor or controller 33 with Wi-Fi, or local area wireless technology that allows the endotracheal tube insertion device 30 to participate in computer networking. The processor or controller 33 may also have Bluetooth capability to allow a medical specialist to view, via the internet, any video images captured by the optical assembly 36. If desired, the controller 33 may be provided as a part of the video monitor 40, or at any other desired location in the improved endotracheal tube insertion device 30. Alternatively, in lieu of the handle 32, the handle and viewing member described in U.S. Pat. No. 7,563,227 may be provided.

The blade assembly 34 has an insertion member configured as an elongated blade body 35 attached to a channel member 37, as best shown in FIGS. 3 and 4. The elongated blade body 35 includes a first or distal end 35a, and a second or proximal end 35b attached to the handle 32. As shown in FIGS. 3 and 4, the blade body 35 is substantially straight in the longitudinal direction and has an arcuate cross-sectional shape.

The channel member 37 includes a first or distal end 37a, and a second or proximal end 37b, defines a longitudinally extending channel 37c, and is attached to a first side 35c (lower side when viewing FIGS. 2 and 4) of the blade body 35. As also shown in FIG. 4, the channel member 37 is substantially C-shaped when viewed in cross-section and defines an elongated slot 37b that provides access to the channel 37c. Alternatively, the channel member 37 may have any desired cross-sectional shape, such as substantially oval, and substantially rectangular.

When viewed from the bottom of the blade body 35, as shown in FIG. 3, the channel 37c of the channel member 37 opens toward a first edge 35e1 of the blade body 35 (the upper edge when viewing FIG. 3). Alternatively, the channel 37c of the channel member 37 may open in any desired direction, such as toward a second edge 35e2 of the blade body 35 (the lower edge when viewing FIG. 3). As also shown in FIG. 3, the channel member 37 is positioned near the first edge 35e1 of the blade body 35 (the upper edge when viewing FIG. 3). Alternatively, the channel member 37 may be positioned near the second edge 35e2 of the blade body 35 (the lower edge when viewing FIG. 3), or at any position intermediate the first edge 35e1 and the second edge 35e2.

The blade body 35 may have any desired length, such as a length within the range of from about 8 cm to about 20 cm. Alternatively, the blade body 35 may be shorter than about 8 cm or longer than about 20 cm. The blade body 35 and the channel member 37 may be formed from any desired rigid or semi-rigid material, such as stainless steel and polyvinyl chloride (PVC). In the illustrated embodiment, the distal end 37a of the channel member 37 is spaced a short distance apart from the distal end 35a of the blade body 35, and the proximal end 37b of the channel member 37 terminates at the proximal end of the 35b of the blade body. The distal end 37a of the channel member 37 may be positioned at any desired distance from the distal end 35a of the blade body 35. If desired, the proximal end 37b of the channel member 37 may terminate prior to the proximal end of the 35b of the blade body (to the right of the proximal end of the 35b of the blade body when viewing FIG. 3) or may extend beyond the proximal end of the 35b of the blade body (to the left of the proximal end of the 35b of the blade body when viewing FIG. 3). The illustrated blade assembly 34 includes the substantially straight blade body 35. Alternatively, the blade assembly 34 may be formed with the curved blade body 44, described in detail below.

If desired, endotracheal tube retention tabs may be provided on the blade assembly 34 of the endotracheal tube insertion device 30. For example, as shown in FIG. 2, two endotracheal tube retention tabs 39a extend outwardly and upwardly (when viewing FIG. 2) from the channel member 37 and one endotracheal tube retention tab 39b extends outwardly and downwardly (when viewing FIG. 2) from the handle 32. The endotracheal tube retention tabs 39a and 39b have a generally arcuate shape and are configured to allow the endotracheal tube 92 to be temporarily positioned and retained between the endotracheal tube retention tabs 39a and the endotracheal tube retention tab 39b. Alternatively, the tracheal tube retention tabs 39a and 39b may have any other desired shape suitable for retaining the endotracheal tube 92. Like the blade body 35 and the channel member 37, the endotracheal tube retention tabs 39a and 39b may be formed from any desired rigid or semi-rigid material, such as stainless steel and polyvinyl chloride (PVC). It will be understood that any desired number of endotracheal tube retention tabs 39a and 39b may be provided. Further, the endotracheal tube retention tabs 39a and 39b may be provided at any desired location on the blade assembly 34 and/or the handle 32.

Referring to FIG. 11, a second embodiment of the blade assembly is shown at 42 attached to the handle 32. The blade assembly 42 has an elongated and upwardly curved blade body 44 attached to a channel member 46. The blade body 44 includes a first or distal end 44a, and a second or proximal end 44b attached to the handle 32. Like the blade body 35, the blade body 44 has an arcuate cross-sectional shape.

The channel member 46 is attached to a first side 44c (lower side when viewing FIG. 11) of the blade body 44, includes a first portion 46a and a second portion 46b, and defines a longitudinally extending channel 46c. The channel member 46 is substantially C-shaped when viewed in cross-section and defines an elongated slot 46d that provides access to the channel 46c. Alternatively, the channel member 46 may have any desired cross-sectional shape, such as substantially oval, and substantially rectangular. The second portion 46b of the channel member 46 extends beyond the proximal end 44b of the blade body 44 any desired distance, and includes a plurality of notches 48 formed in at least one side of the elongated slot 46d. A distal end of the first portion 46a of the channel member 46 may be positioned at any desired distance from the distal end 44a of the blade body 44. Like the channel 37c of the channel member 37, the channel 46c of the channel member 46 may open in any desired direction relative to the blade body 44, and may be laterally positioned near either longitudinal edge of the blade body 44, or any position intermediate thereof. The illustrated blade assembly 42 includes the curved blade body 44. Alternatively, the blade assembly 42 may be formed with the substantially straight blade body 35, described in detail above.

If desired, endotracheal tube retention tabs may also be provided on the blade assembly 42. For example, as shown in FIG. 11, two endotracheal tube retention tabs 49a extend outwardly and upwardly (when viewing FIG. 11) from the channel member 46 and one endotracheal tube retention tab 49b extends outwardly and downwardly (when viewing FIG. 11) from the handle 32. The endotracheal tube retention tabs 49a and 49b have a generally arcuate shape and are configured to allow the endotracheal tube 92 to be temporarily positioned and retained between the endotracheal tube retention tabs 49a and the endotracheal tube retention tab 49b. Alternatively, the endotracheal tube retention tabs 49a and 49b may have any other desired shape suitable for retaining the endotracheal tube 92. Like the endotracheal tube retention tabs 39a and 39b, the endotracheal tube retention tabs 49a and 49b may be formed from any desired rigid or semi-rigid material, such as stainless steel and polyvinyl chloride (PVC). It will be understood that any desired number of endotracheal tube retention tabs 49a and 49b may be provided. Further, the endotracheal tube retention tabs 49a and 49b may be provided at any desired location on the blade assembly 42 and/or the handle 32.

Figure 5:
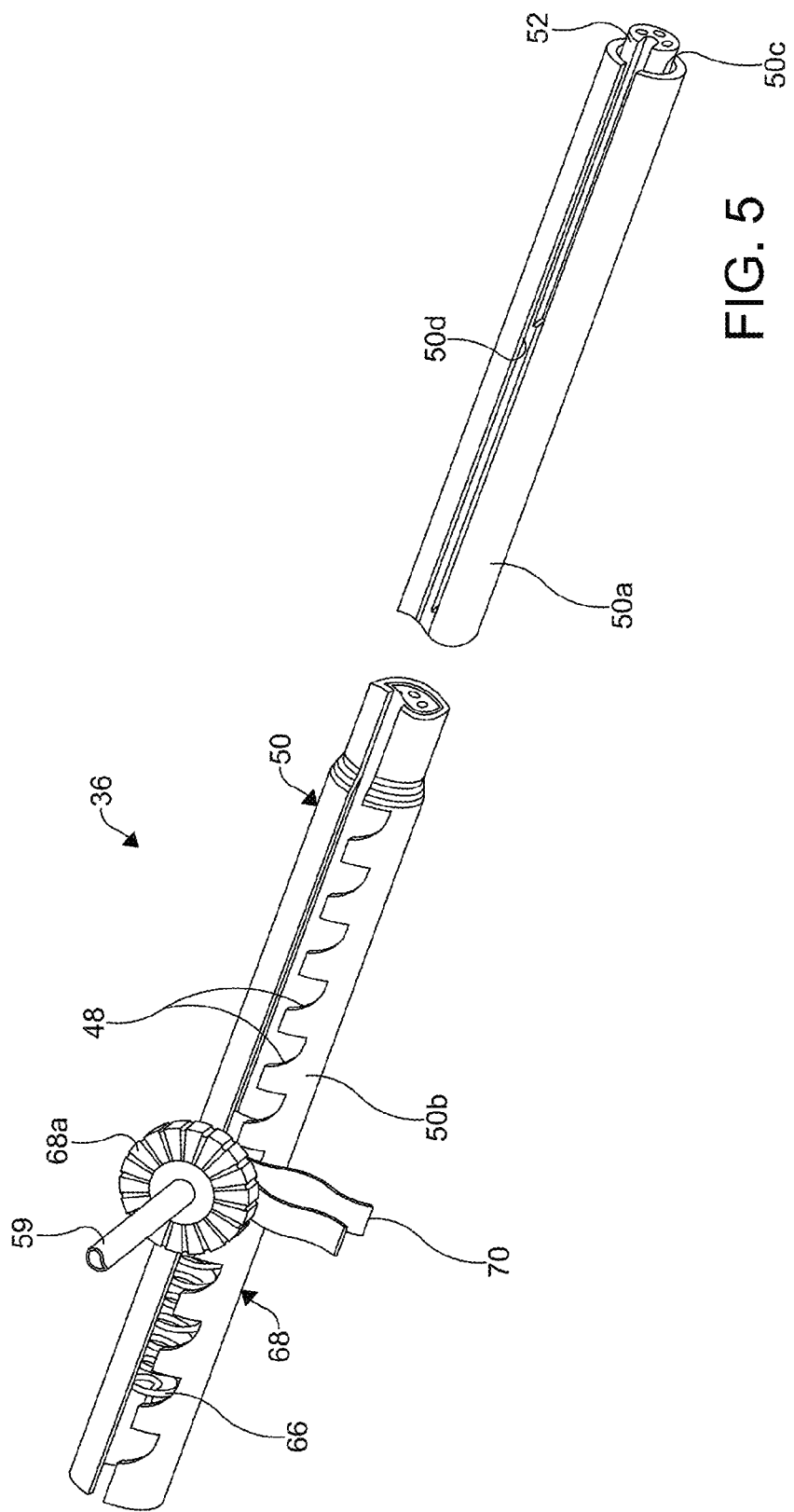
FIG. 5 is a perspective view of the optical assembly illustrated in FIGS. 2 and 3.
Figure 6:
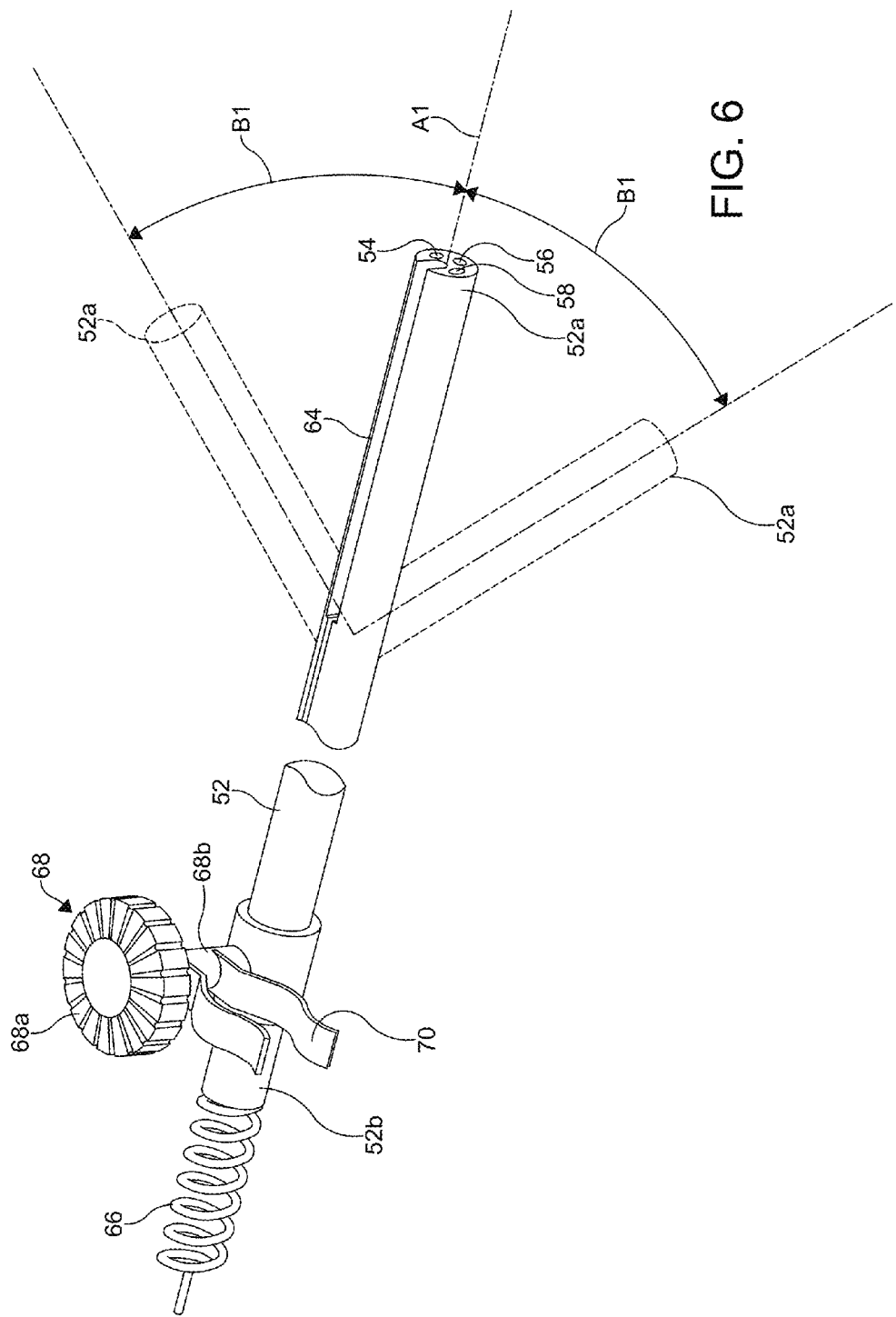
FIG. 6 is a perspective view of the optical assembly illustrated in FIG. 5 showing the optical housing removed.

As shown in FIG. 2, the optical assembly 36 is disposed within the channel 37c of the channel member 37. As best shown in FIGS. 5 through 7, the optical assembly 36 includes an optical housing 50 and the flexible member 52. The illustrated optical housing 50 includes a first portion 50a and a second portion 50b, and defines a longitudinally extending channel 50c. The optical housing 50 is substantially circular when viewed in cross-section and defines an elongated slot 50d that provides access to the channel 50c. Alternatively, the optical housing 50 may have any desired cross-sectional shape, such as substantially oval. In the illustrated embodiment of the optical housing 50, an inside diameter of the second portion 50b of the optical housing 50 is larger than an inside diameter of the first portion 50a. Alternatively, the inside diameter of the second portion 50b may be smaller than or equal to the inside diameter of the first portion 50a. The second portion also includes a plurality of the notches 48 formed in at least one side of the elongated slot 50d. The optical housing 50 may be formed from any desired rigid or semi-rigid material, such as PVC, wire-reinforced silicon, and stainless steel. Additionally, the optical housing 50 may be configured to be relatively more flexible at a portion of the optical housing 50 between the first and second portions 50a and 50b, thus allowing the user to bend the portion of the optical housing 50 that extends between the channel member 37 and the video monitor 40, as shown in FIG. 2.

Although the blade assembly 34 of the illustrated improved endotracheal tube insertion device 30 is shown having the channel member 37 attached thereto, the channel member 37 is not required. For example, the first portion 50a of the optical housing 50 illustrated in FIG. 5 may be attached to the first side 35c (lower side when viewing FIGS. 2 and 4) of the blade body 35 in the same manner that the channel member 37 is attached. In such an embodiment, the longitudinally extending channel 50c would function in the same manner as the longitudinally extending channel 37c of the channel member 37.

Figure 7:
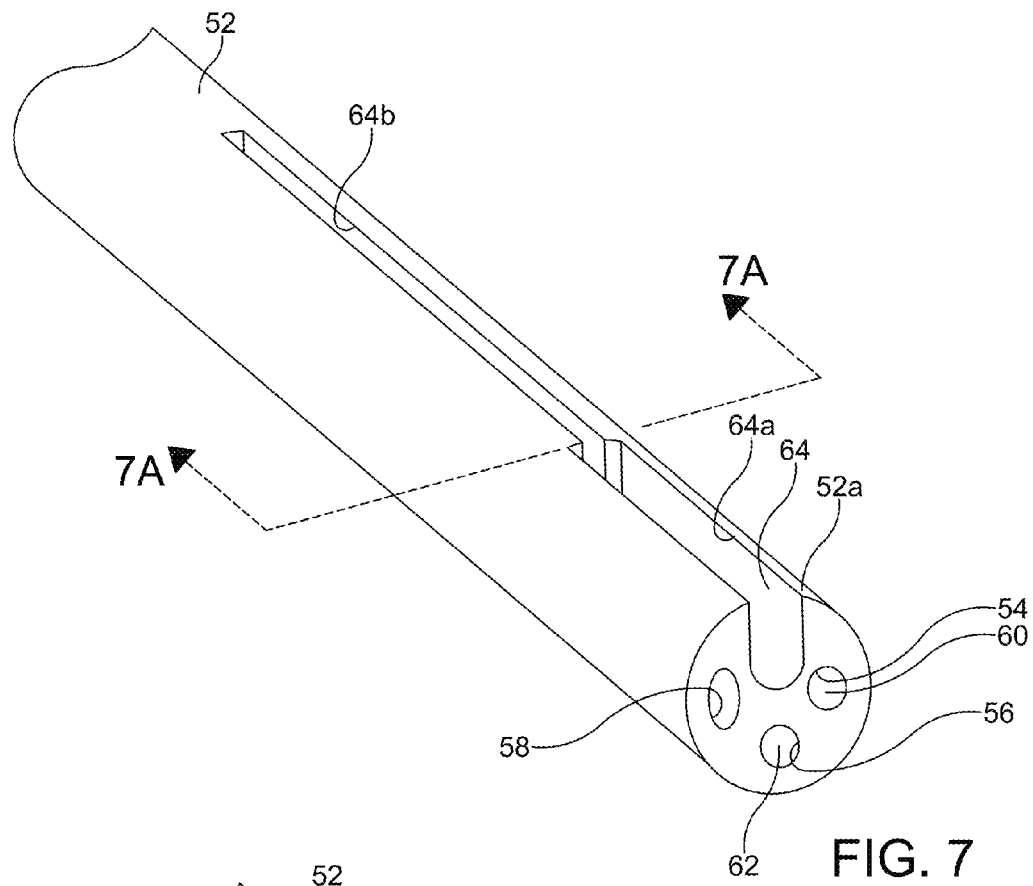
FIG. 7 is an alternate perspective view of the optical assembly illustrated in FIG. 6.

As best shown in FIGS. 6 and 7, the flexible member 52 is an elongated member having an axis A1, a substantially cylindrical shape and includes a first or distal end 52a and a second or proximal end 52b. Alternatively, the flexible member 52 may have any other desired cross-sectional shape, such as substantially oval, substantially hexagonal, and substantially rectangular. A plurality of longitudinally extending conduits is formed within the flexible member 52. As shown in FIG. 7, the flexible member 52 includes a first longitudinally extending conduit 54, a second longitudinally extending conduit 56, and a third longitudinally extending conduit 58. The video imaging device 60 is disposed in the first longitudinally extending conduit 54. In the illustrated embodiment, the video imaging device 60 is a Complementary Metal Oxide Silicon (CMOS) camera. Alternatively, the video imaging device 60 may be any desired video imaging device, such as a Charge-Coupled Device (CCD), fiber optic camera, and any other direct or indirect imaging device.

A light source 62 is disposed in the second longitudinally extending conduit 56. In the illustrated embodiment, the light source 62 is an LED lamp or an incandescent bulb mounted at the distal end 52a of the flexible member 52. Alternatively, the light source 62 may be any other source of light. Additionally, the light source 62 may be a fiber optic cable connected at its proximal end to a source of illumination (not shown), such as an LED lamp, an incandescent bulb, or any other desired light source. The video imaging device 60 and the light source 62 are operationally connected to the video monitor 40 and/or the controller 33 by one or more flexible electrical and/or optical connectors, shown at 66 in FIG. 6.

The third longitudinally extending conduit 58 is configured as a suction tube and is connected to a vacuum port, such as a vacuum port 59 extending outward of the knob 68a, as shown in FIG. 5. Although described as a suction tube, the conduit 58 may also be used to provide oxygen to a patient. The conduit 58 may further be used to introduce tools, such as medical instruments (not shown) into the patient. In the illustrated embodiment, the flexible member 52 has an outside diameter of about 4 mm. Alternatively, the flexible member 52 may have any other outside diameter.

Figure 7A:
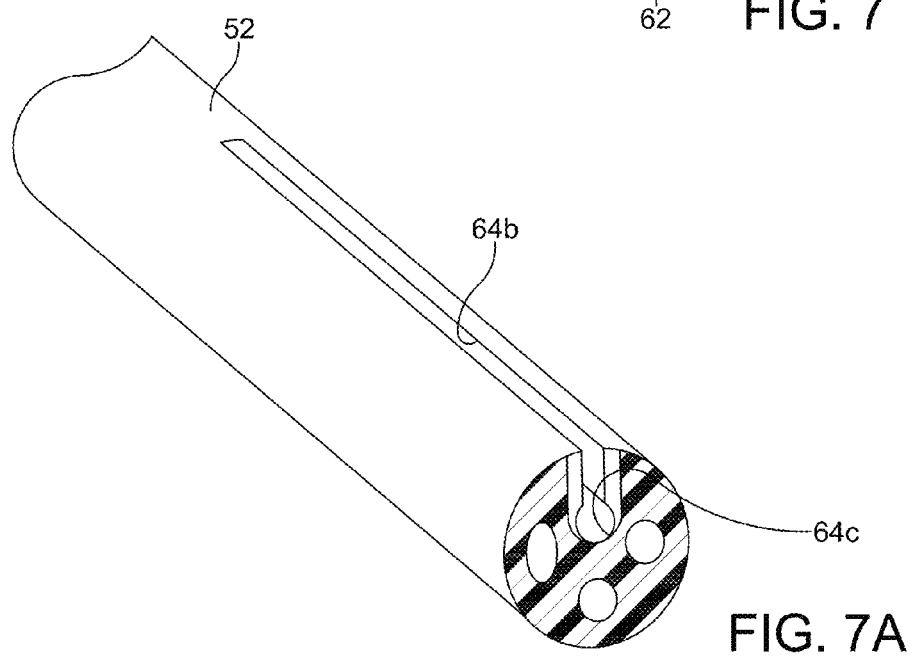
FIG. 7A is a cross-sectional view taken along the line 7A-7A of FIG. 7.

The distal end 52a of the flexible member 52 also includes an intubation assembly guide channel 64, the purpose for which will be described below. The illustrated intubation assembly guide channel 64 includes a first portion 64a, a second portion 64b proximal of the first portion 64a, and a third portion 64c adjacent to, and radially inward of, the second portion 64b, as shown in FIG. 7A. In the illustrated embodiment, the third portion 64c is wider than the second portion 64b for reasons that will be described below. Specifically, the third portion 64c is substantially cylindrical and has an inside diameter about the same size at an outside diameter of an elongated guide member portion 78 of a guide rail 75, described below. Alternatively, the third portion 64c may have any other desired cross-sectional shape, such as substantially oval, substantially hexagonal, and substantially rectangular. If desired, the third portion 64c may have any desired inside diameter, such as an inside diameter larger than the outside diameter of the guide member portion 78 of the guide rail 75. Additionally, the first portion 64a has a relatively wide longitudinal opening and the second portion 64b has a longitudinal opening smaller than the longitudinal opening of the first portion 64a.

In the illustrated embodiment, the intubation assembly guide channel 64 has a length within the range of about 3 cm to about 7 cm, the first portion 64a has a length within the range of about 0.5 cm to about 2 cm, and the second and third portions 64b and 64c have a length within the range of about 2 cm to about 5 cm. Alternately, the intubation assembly guide channel 64, and each of the first, second, and third portions 64a, 64b, and 64c may have any desired length and width.

Further, it will be understood that the flexible member 52 maybe formed without the relatively wide first channel portion 64a, and with only the second and third portions 64b and 64c, such as shown in FIG. 7A. In an embodiment of the flexible member 52 having only the second and third portions 64b and 64c of the intubation assembly guide channel 64, each of the second and third portions 64b and 64c may have any desired length, such as a length within the range of about 2 cm to about 7 cm.

In the illustrated embodiment, the first and second longitudinally extending conduits 54 and 56 have a circular cross sectional shape, and the third longitudinally extending conduit 58 has an oval cross sectional shape. Alternatively, the first, second, and third longitudinally extending conduits 54, 56, and 58 may have any desired cross sectional shape. The flexible member 52 may be formed from any desired flexible or semi-flexible material, such as silicon, rubber, wire-reinforced silicon, wire-reinforced rubber, and polymers. Additionally, the flexible member 52 may be configured to be relatively more flexible at its distal end 52a and relatively less flexible at its proximal end 52b, thus providing greater flexibility within a patient's airway, and less flexibility, and therefore greater control, for the user when handling the proximal end 52b.

The distal end 52a of the flexible member 52 also includes a mechanism (not shown) for moving a portion of the distal end 52a, so as to view desired portions of the patient's air passage. The mechanism may be mechanically or electrically actuated, and is configured to move the distal end 52a through an angle B1. In the illustrated embodiment, the angle B1 is about +/−90 degrees from the axis A1 of the flexible member 52. Additionally, the distal end 52a of the flexible member 52 may also be configured to move in any radial direction.

The mechanism for moving a portion of the distal end 52a may be controlled by a control device 68 at the proximal end 52b of the flexible member 52. The illustrated control device 68 includes the rotatable knob 68a and a mounting post 68b. Alternatively, the control device 68 may located at any other desired location on the flexible member 52 or any other desired location on the improved endotracheal tube insertion device 30. The mechanism for moving a portion of the distal end 52a, and therefore the movement of the distal end 52a of the flexible member 52, may be controlled by the control device 68, thus allowing the user to move the distal end 52a of the flexible member 52 to a desired location and to lock or retain the distal end 52a in the position selected by the user. As shown in FIGS. 5 through 7, an attachment member 70 is attached to the mounting post 68b of the control device 68. The attachment member 70 may be any device configured to retain the guided introducer intubation assembly 38 and its attached endotracheal tube 92, described below, relative to the improved endotracheal tube insertion device 30, and more specifically relative to the flexible member 52. Alternatively, the attachment member 70 may be mounted to any desired portion of the improved endotracheal tube insertion device 30, including the handle 32 and the video monitor 40.

Figure 8A:
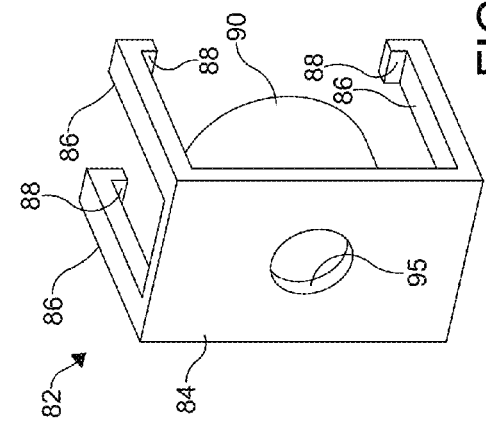
FIG. 8A is a cross-sectional view taken along the line 8A-8A of FIG. 8.

The guided introducer intubation assembly 38 includes an intubation assembly body configured as a rod 72, best shown in FIGS. 8 and 8A, which defines an introducer or bougie. The rod 72 is substantially cylindrical and has an elongated body having a first or distal end 72a and a second or proximal end 72b. Alternatively, the rod 72 may have any other desired cross-sectional shape, such as substantially oval, substantially hexagonal, and substantially rectangular. The distal end 72a of the rod 72 is tapered or substantially cone-shaped and defines a leading end of the rod 72. The rod 72 includes a plurality of longitudinally and radially outwardly extending ribs 74. In the illustrated embodiment, the rod 72 is shown prior to being inserted into the endotracheal tube 92, such as the endotracheal tube 92 shown in FIG. 9. As shown, the ribs 74 have an arcuate cross-sectional shape. The ribs 74 may extend for any desired length of the rod 72 and taper toward the distal end 72a.

The illustrated rod 72 includes a guide system configured to guide the endotracheal tube 92 into the trachea, and configured for releasable attachment to the flexible member 52 of the optical assembly 36. In the illustrated embodiment, the guide system is a guide rail 75. The illustrated guide rail 75 includes a substantially spherical tip 76 at a distal end of the guide member portion 78. The guide member portion 78 may be attached to the rod 72 by a substantially flat bridge 80 that extends between the rod 72 and the guide member portion 78. Alternatively, the guide member portion 78 may be attached directly to the rod 72 without the bridge 80. Although illustrated as spherical, the tip 76 may have other shapes, such as substantially ovoid, or having the shape of a rectangular prism or a triangular prism. It will be understood that the tip 76 is not required, and the distal end of the guide member portion 78 may have a rounded or tapered surface. Additionally, the tip 76 may be of any size and have any shape that fits within the first portion 64a. Further, the guide member portion 78 is configured to fit within the third portion 64c, and has a diameter large enough that it is laterally retained, i.e., that it cannot fall or be otherwise laterally removed through the second portion 64b of the guide channel 64. In the illustrated embodiment, the guided introducer intubation assembly 38 has an overall length within the range of about 40 cm to about 50 cm. Alternatively, the guided introducer intubation assembly 38 may have any other desired length.

As best shown in FIG. 8, the guide member portion 78 guide member portion 78 has a substantially cylindrical shape and a length L1, measured from the spherical tip 76, of about 5 cm. Alternatively, the guide member portion 78 may have any other desired cross-sectional shape, such as substantially oval, substantially hexagonal, and substantially rectangular. Further, the guide member portion 78 may have any desired length L1, such as a length from about 4 cm to about 6 cm. The illustrated bridge 80 extends from a point near the spherical tip 76 to a point near a proximal end of the guide member portion 78. The bridge 80 may have any width and length, and may be attached to the guide member portion 78 at any point proximal to the spherical tip 76 or proximal to a distal end of the guide member portion 78 if the guide member portion 78 is formed without the tip 76. Alternatively, the bridge 80 may be located at any desired portion of the rod 72. The substantially cylindrically shaped portion of the rod 72 thus begins at a point about 7 cm from the spherical tip 76. Alternatively, the substantially cylindrically shaped portion of the rod 72 may begin at any desired distance from the spherical tip 76, such as a distance from about 6 cm to about 8 cm. The bridge 80 may have any desired thickness such that the bridge 80 may extend through the second portion 64b of the guide channel 64, as described in detail below.

The rod 72 and the ribs 74 formed thereon, and the guide rail 75 and its component parts; i.e., the guide member portion 78, the substantially spherical tip 76, and the bridge 80, may be formed from any flexible or semi-flexible material, such as silicon, rubber, wire-reinforced silicon, and wire-reinforced rubber. Additionally, the rod 72 may be configured to be relatively more flexible at its distal end 72a and relatively less flexible at its proximal end 72b, thus providing greater flexibility within a patient's airway, and less flexibility, and therefore greater control, for the user when handling the proximal end 72b.

If desired, in lieu of the ribs 74, the ribbed portion of the rod 72 may be configured as a hollow inflatable member, wherein the inflatable portion of the rod 72 may be inflated to a desired outside diameter corresponding to inside diameter of an endotracheal tube 92. Alternatively, the improved endotracheal tube insertion device 30 may be provided with a plurality of rods 72, each with ribs 74 having a different outside diameter corresponding to the inside diameter of one of a plurality of endotracheal tubes 92 having different inside diameters. Additionally, the improved endotracheal tube insertion device 30 may be provided with a plurality of rods 72 formed without ribs, each of the plurality of rods having a different outside diameter corresponding to the inside diameter of one of a plurality of endotracheal tubes 92 having different inside diameters. It will be understood that each embodiment of the rod described herein, including the embodiment of the rod having the hollow inflatable member described above, may be formed with the tapered or substantially cone-shaped leading end as described above and illustrated, for example, at 72a in FIG. 8.

The flexible or semi-flexible material and arcuate cross-sectional shape of the ribs 74 allow the ribs to be generally flexible; i.e., radially compressible such that the outside diameter of the ribs may vary and such that the rod 72 may be used in endotracheal tubes 92 having varying inside diameters, such as inside diameters from about 3.0 mm, or the size of a conventional pediatric endotracheal tube 92, to about 9.0 mm, or the size of a convention adult endotracheal tube 92. Alternatively, the endotracheal tube 92 may have an inside diameter smaller than about 3.0 mm or larger than about 9.0 mm. Preferably, the ribs 74 will engage the inside surface of the endotracheal tube 92 in which the rod 72 has been inserted, whether the inside surface has a small inside diameter, such as about 3.0 mm or a larger inside diameter, such as about 9.0 mm.

Figure 8B:
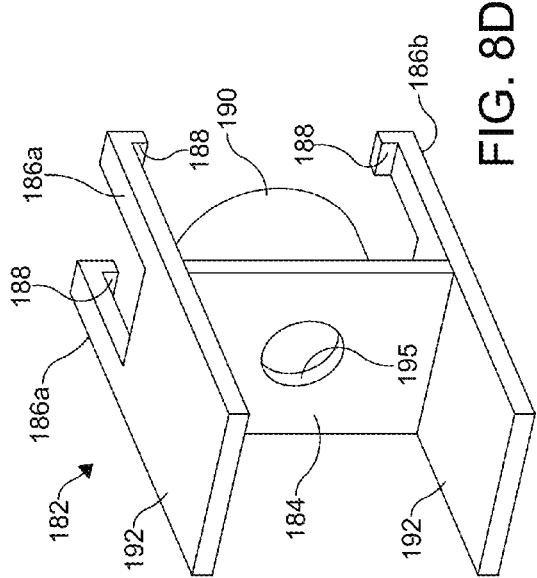
FIG. 8B is an enlarged perspective view of a first embodiment of the first connecting member illustrated in FIG. 8.

The proximal end 72b of the rod 72 includes threads 73 configured for connecting the rod 72 to a first connecting member 82, shown in FIGS. 8 and 8B. The first connecting member 82 includes a base 84 having a plurality of arms 86 extending outward therefrom. The arms 86 include inwardly extending flanges or locking members 88. A substantially cylindrical body 90 also extends outwardly from the base 84 between the arms 86. A longitudinally extending threaded channel 95 is formed at least through the base 84. The first connecting member 82 is configured to be attached to the threads 73 of the rod 72. This threaded connection allows the user to adjust the longitudinal position of the first connecting member 82 relative to the rod 72, i.e., in the direction of the arrow 93 in FIG. 8, by rotating the attachment first connecting member 82 clockwise or counterclockwise. This threaded connection further allows the user to shorten or lengthen the rod 72 relative to the length of the tube body 94 of the endotracheal tube 92 that will be mounted on the rod 72. If desired, a portion of the proximal end 72b of the rod 72 that extends outward of the first connecting member 82 may be removed by the user, such as by cutting. It will be understood that the rod 72 may be shortened or lengthened relative to the length of the tube body 94 by any other means.

Figure 8C:
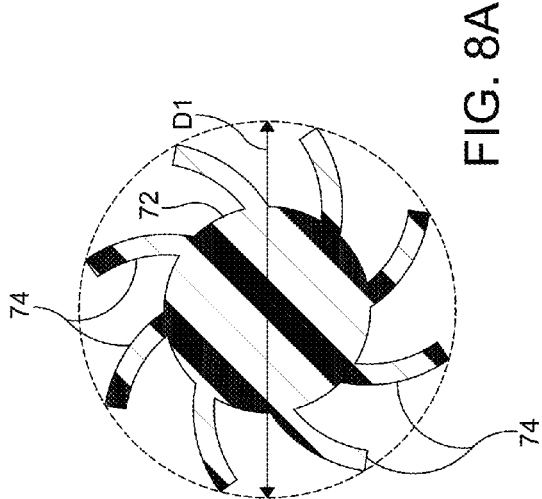
FIG. 8C is an elevational view of an alternate embodiment of the first connecting member illustrated in FIGS. 8 and 8A.

Referring to FIG. 8C, a first alternate embodiment of the first connecting member is shown at 82'. The first connecting member 82' is similar to the first connecting member 82, however, the cylindrical body 90 of the first connecting member 82' includes a portion 90a extending outward of the base 84 for connection to a source of oxygen for example. The portion 90a may have any desired inside and outside diameter, and may have any desired length, which may include a length equal to a length of the cylindrical body 90. Alternatively, the portion 90a may have a length shorter or longer than a length of the cylindrical body 90. The portion 90a may be configured for attachment to a source of oxygen or air, in the same manner that the cylindrical body 98b of the conventional connector 98 shown in FIG. 9 is configured for attachment to a source of oxygen or air.

If desired, air flow passageways 91 may be formed through base 84 within the portion 90a, as shown in FIG. 8C. The air flow passageways 91 define a flow path for oxygen or air from the source of oxygen or air to the endotracheal tube 92.

Figure 8D:
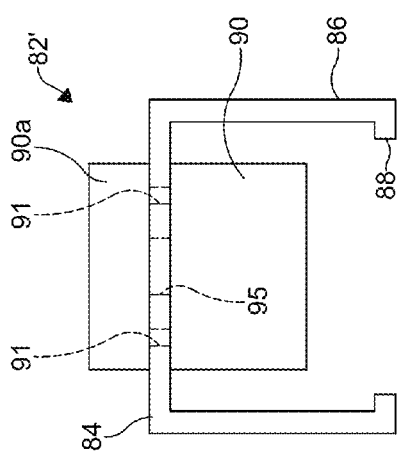
FIG. 8D is an enlarged perspective view of a second embodiment of the first connecting member illustrated in FIG. 8.

Referring to FIG. 8D, a second alternate embodiment of the first connecting member is shown at 182. The first connecting member 182 is similar to the first connecting member 82, and includes a base 184 having a plurality of arms 186 extending outward therefrom. The illustrated embodiment of the first connecting member 182 includes a first pair of arms 186a and a second pair of arms 186b, only one of which is shown in FIG. 8D, opposite the first pair of arms 186a. Each of the arms 186a and 186b include inwardly extending locking members 188. A substantially cylindrical body 190 also extends outwardly from the base 184 between the arms 186a and 186b. A longitudinally extending threaded channel 195 is formed in the base 184. Side walls 192 extend outwardly from the base 184 in a direction away from the arms 186a and 186b at side edges of the base 184. The side walls 192 are extensions of the arms 186a and 186b and define opening tabs that, when compressed or urged toward one another, such as by the user, the first pair of arms 186a and the second pair of arms 186b are urged away from each other, thus allowing the user to more easily attach and detach the flange 98a of the connector 98 from the first connecting member 182. If desired, the side walls 192 may be formed on any of the embodiments of the first connecting member, such as the first connecting members 82 and 82'.

Figure 9:
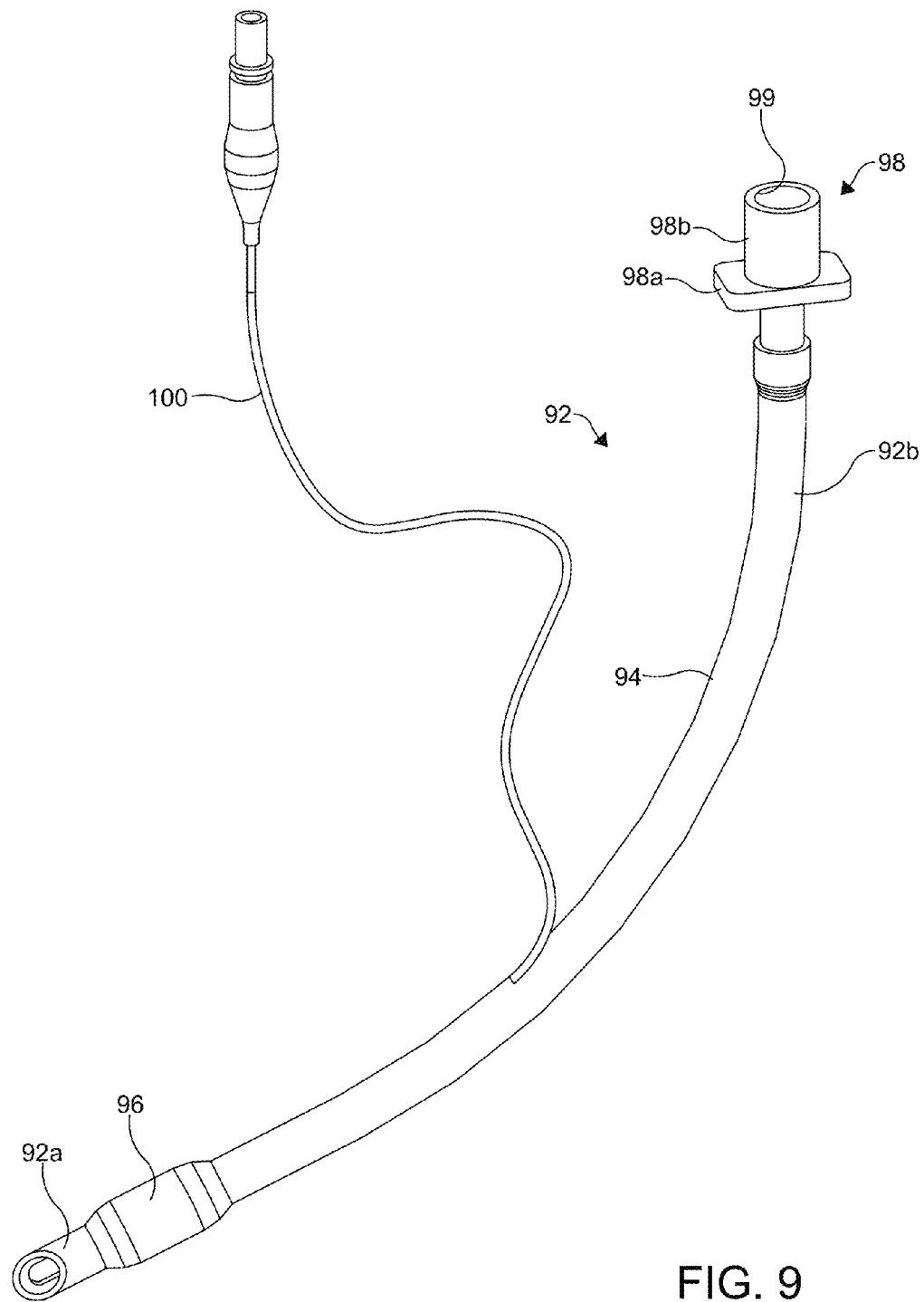
FIG. 9 is a perspective view of the conventional endotracheal tube illustrated in FIGS. 2 and 3.

The guided introducer intubation assembly 38 further includes a conventional endotracheal tube, such as shown at 92 in FIG. 9. The endotracheal tube 92 is configured for attachment to the rod 72, as best shown in FIG. 2. The endotracheal tube 92 has a first or distal end 92a and a second or proximal end 92b. The endotracheal tube 92 further includes a tube body 94 having balloon cuff 96 at the distal end 92a, and a conventional connector 98 at the proximal end 92b thereof. As described in detail above, the tube body 94 of the endotracheal tube 92 may have an inside diameter of from about 3.0 mm to about 9.0 mm.

The connector 98 includes a flange 98a having a substantially cylindrical body 98b extending outwardly from the flange 98a. The body 98b has a longitudinally extending channel 99 formed therethrough. An air inflation tube 100 is attached to the balloon cuff 96 and configured for attachment to a source of air, such as a syringe.

The connector 98 is configured for attachment to the first connecting member 82. When attached, the body 98b is inserted into the body 90 of the first connecting member 82 and the flange 98a is snap fit between the arms 86 and retained between the arms 86 by the locking members 88. The body 98b of the connector 98 has an outside diameter of about 15 mm. Alternatively, the body 98b may have any other outside diameter. If desired, the conventional connector 98 and the first connecting member 82 may be configured such that the body 90 of the first connecting member 82 is smaller than, and may be inserted into the body 98b of the connector 98.

When the guided introducer intubation assembly 38 is assembled, the rod 72 is inserted through the channel 99 of the connector 98 and into the tube body 94 of the conventional endotracheal tube 92 until the guide member portion 78 extends outward of the distal end 92a of the endotracheal tube 92. When the rod 72 is mounted within the tube body 94 of the endotracheal tube 92, the longitudinally extending spaces between the ribs 74 define flow paths for oxygen from a source of oxygen (not shown) to the patient during intubation and before the guided introducer intubation assembly 38 is removed.

Although not illustrated, the rod 72 may be formed as a hollow member and may also have one or more radially extending holes or perforations along its length to facilitate the delivery and flow of oxygen from the proximal end 72b of the rod 72.

Advantageously, the improved endotracheal tube insertion device 30, and particularly the shape and tapered leading edge of the ribs 74 (or the alternative ribbed portion of the rod 72 configured as a hollow inflatable member), the smooth, tapered or cone-shaped leading end 72a of the rod 72. the spherical tip 76, and the guide member portion 78 of the improved guided introducer intubation assembly 38 is configured to avoid being caught on laryngeal structures as the guided introducer intubation assembly 38 and the leading edge or distal end 92a of the endotracheal tube 92 is advanced into the patient's airway, thus facilitating the delivery of the endotracheal tube 92 between the vocal cords and preventing trauma or injury to the vocal cords and other parts of the airway.

Figure 10:
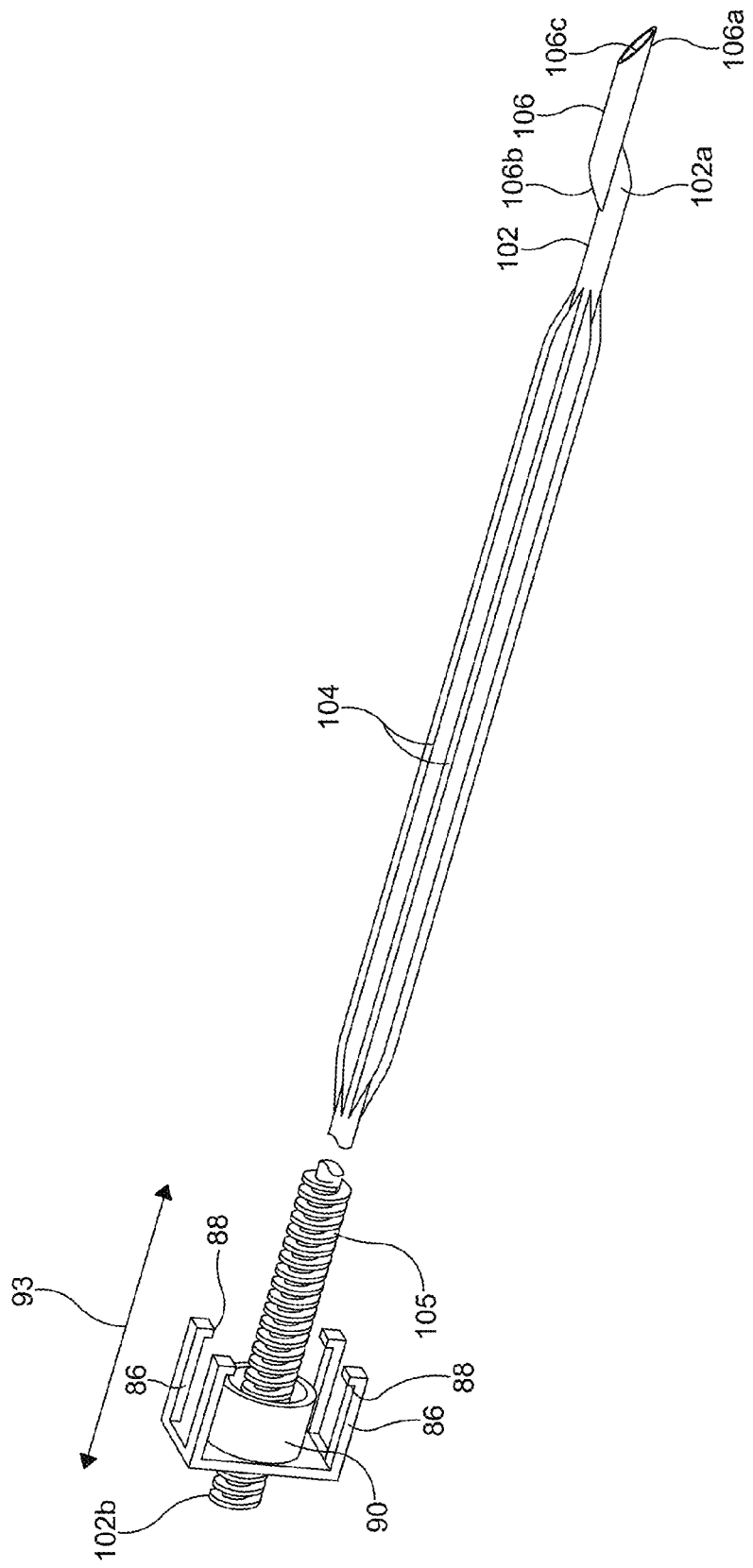
FIG. 10 is a plan view of a second embodiment of the intubation assembly rod illustrated in FIG. 8.

A second embodiment of the intubation assembly rod is shown at 102 in FIG. 10. The rod 102 is similar to the rod 72 and includes the plurality of longitudinally and radially outwardly extending ribs 104. The proximal end 102b of the rod 102 also includes threads 105 configured for connecting the rod 102 to the first connecting member 82, described above.

The distal end 102a of the rod 102 is tapered or substantially cone-shaped and defines a leading end of the rod 102, and includes a guide system configured as a guide sleeve 106 in lieu of the guide member portion 78 and the spherical tip 76 of the guide rail 75. The guide sleeve 106 includes a first or distal end 106a, a second or proximal end 106b, and has a longitudinally extending substantially cylindrical channel 106c formed therethrough. The illustrated guide sleeve 106 is mounted directly to the rod 102 and a bridge, such as the bridges 80 and 112, are not required, but may be provided if desired.

In the illustrated embodiment, the distal and proximal ends 106a and 106b are tapered. The guide sleeve 106 is configured such that either the optical housing 50 or the flexible member 52, as best shown in FIG. 12, may be inserted through the channel 106c and that the guide sleeve 106 can be slidably mounted within the channel member 37. Advantageously, the tapered leading or distal end 106a of the guide sleeve 106 is also configured for easy and atraumatic advancement into the patient's airway; i.e., configured to avoid being caught on laryngeal structures as the guided introducer intubation assembly 38 and the leading edge or distal end 92a of the endotracheal tube 92 is advanced into the patient's airway, thus facilitating the delivery of the endotracheal tube 92 between the vocal cords and preventing trauma or injury to the vocal cords and other parts of the airway.

A third embodiment of the intubation assembly rod is shown at 108 in FIG. 12. The distal end 108a of the rod 108 is tapered or substantially cone-shaped and defines a leading end of the rod 108. The rod 108 includes a guide sleeve 110. The guide sleeve 110 includes a first or distal end 110a, a second or proximal end 110b, and has a longitudinally extending substantially cylindrical channel 110c formed therethrough. The guide sleeve 110 is attached to the rod 108 by a substantially flat bridge 112 that extends between the rod 108 and the guide sleeve 110. The rod 108 is otherwise substantially the same as the rod 102. Like the bridge 80, the bridge 112 may be located at any desired portion of the rod 108. The bridge 112 may have any width and length, and may be attached to the guide sleeve 110 at any point proximal to the distal end 110a of the guide sleeve 110. Further, the guide sleeve 110 may be attached to the rod 108 at any other longitudinal location or at any other desired distance from the distal end 108a of the rod 108. The guide sleeve 110 is configured such that the distal end 52a of the flexible member 52, as shown in FIG. 12, may be inserted through the channel 110c. The guide sleeve 110 is further configured for insertion through the channel 50c of the optical housing 50, the channel 37c of the channel member 37, and the channel 46c of the channel member 46. Like the bridge 80, the bridge 112 may have any desired thickness such that the bridge 112 may extend through the slot 50d of the channel 50c, the slot 37b of the channel 37c, and the slot 46d of the channel 46c.

FIG. 12A is an end view of the rod 108 and shows a radially inwardly extending stop member 114 formed at the distal end 110a of the guide sleeve 110. The stop member 114 may be provided to assist in retaining the flexible member 52 within the guide sleeve 110 during insertion of the endotracheal tube insertion device 30 into the patient's airway. Alternatively, the distal end 110a of the guide sleeve 110 may include two or more of the stop members 114. Although shown formed at the distal end 110a of the guide sleeve 110, the stop members 114 may be formed at the proximal end 110b of the guide sleeve 110, or at any location between the distal and proximal ends 110a and 110b. Additionally, the stop members 114 may have any desired shape and size.

Like the guide rail 75 and its component parts, the guide sleeve 110 and the bridge 112 may be formed from any flexible or semi-flexible material, such as silicon, rubber, wire-reinforced silicon, and wire-reinforced rubber.

A fourth embodiment of the intubation assembly rod is shown at 116 in FIG. 13. The distal end 116a of the rod 116 is tapered or substantially cone-shaped and defines a leading end of the rod 116. The rod 116 includes a guide sleeve 118. The guide sleeve 118 includes a first or distal end 118a, a second or proximal end 118b, and has a longitudinally extending substantially cylindrical channel 118c formed therethrough. The guide sleeve 118 is attached to the rod 116 by the substantially flat bridge 112 that extends between the rod 116 and the guide sleeve 118. The illustrated guide sleeve 118 also includes a longitudinally extending slot 120 formed therethrough. The rod 116 is otherwise substantially the same as the rod 102.

A fifth embodiment of the intubation assembly rod is shown at 122 in FIG. 14. The distal end 122a of the rod 122 is tapered or substantially cone-shaped and defines a leading end of the rod 122. The rod 122 includes a guide sleeve 124. The guide sleeve 124 is similar to the guide sleeve 118 and includes a first or distal end 124a, a second or proximal end 124b, and has a longitudinally extending substantially cylindrical channel 124c formed therethrough. The guide sleeve 124 is attached to the rod 122 by the substantially flat bridge 112 that extends between the rod 122 and the guide sleeve 124. Unlike the guide sleeve 118, the distal end 124a of the guide sleeve 124 is not tapered. Rather, an end surface of the distal end 124a is substantially perpendicular to an axis A2 of the guide sleeve 124. The rod 122 is otherwise substantially the same as the rod 102.

Figure 14B:
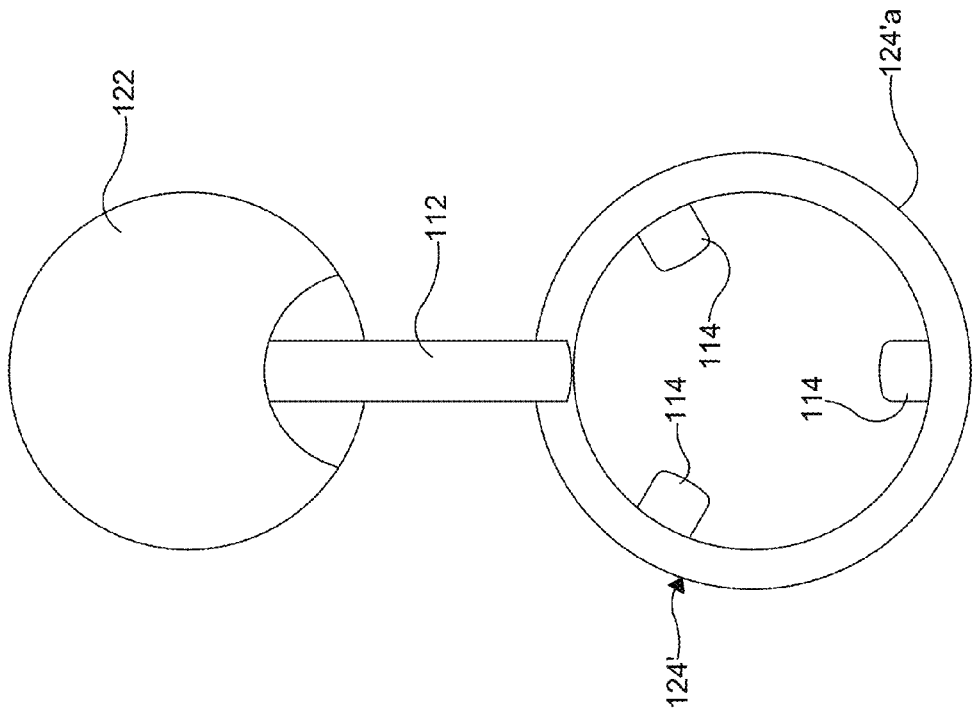
FIG. 14B is an end view of the fifth embodiment of the intubation assembly rod illustrated in FIG. 14 showing a second embodiment of the sleeve and a stop member.
Figure 14A:
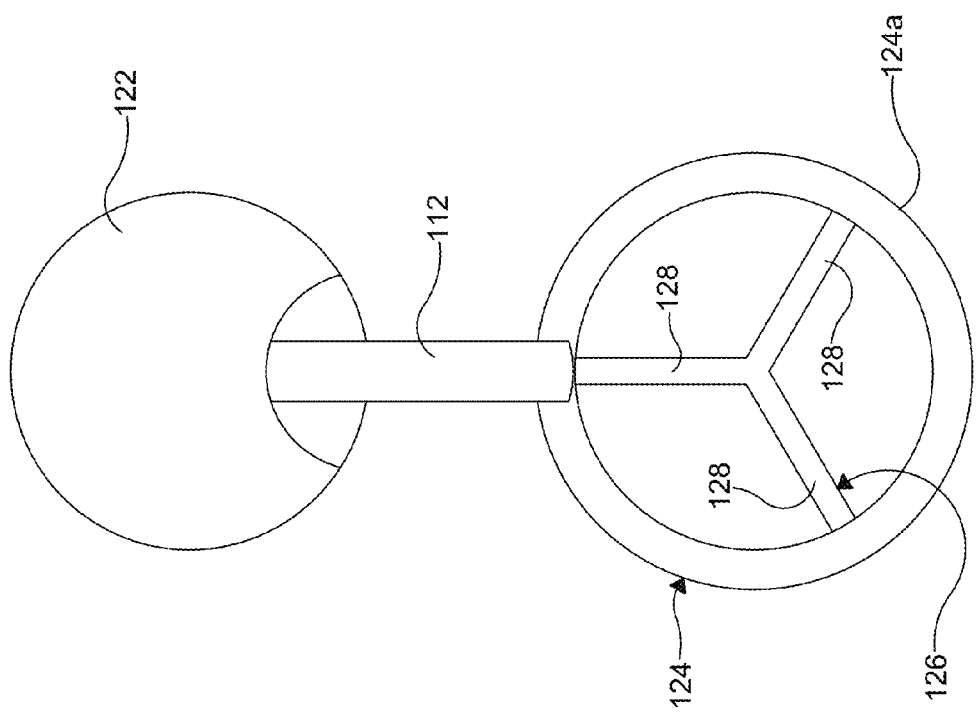
FIG. 14A is an end view of the fifth embodiment of the intubation assembly rod illustrated in FIG. 14 showing a first embodiment of the sleeve and a stop member.

FIG. 14A is an end view of the rod 122 and shows a first embodiment of a stop member 126 formed at the distal end 124a of the guide sleeve 124. The illustrated stop member 126 includes three radially inwardly extending legs 128. The stop member 126 may be provided to assist in retaining the flexible member 52 within the guide sleeve 124 during insertion of the endotracheal tube insertion device 30 into the patient's airway. Alternatively, the distal end 124a of the guide sleeve 124 may include any desired number of the legs 128, such as one, two, or more than three legs 128. Although shown formed at the distal end 124a of the guide sleeve 124, the stop member 126 may be formed at the proximal end 124b of the guide sleeve 124, or at any location between the distal and proximal ends 124a and 124b. Additionally, the legs 128 may have any desired shape and size.

FIG. 14B is an end view of the rod 122 and shows a second embodiment of the guide sleeve 124', wherein the distal end 124'a thereof includes three of the radially inwardly extending stop members 114. As described above, the stop members 114 may be provided to assist in retaining the flexible member 52 within the guide sleeve 124 during insertion of the endotracheal tube insertion device 30 into the patient's airway. Alternatively, the distal end 124'a of the guide sleeve 124' may include two of the stop members 114 or more than three of the stop members 114. Although shown formed at the distal end 124'a of the guide sleeve 124', the stop members 114 may be formed at the proximal end 124'b of the guide sleeve 124', or at any location between the distal and proximal ends 124'a and 124'b. Additionally, the stop members 114 may have any desired shape and size. If desired, an outside surface of the distal end 52a of the flexible member 52 may be formed with guide grooves (not shown) corresponding to the stop members 114. The flexible member 52 would therefore be slidably movable within the guide sleeve 124' and the stop members 114 would slidably engage the flexible member 52 within the grooves.

Figure 15:
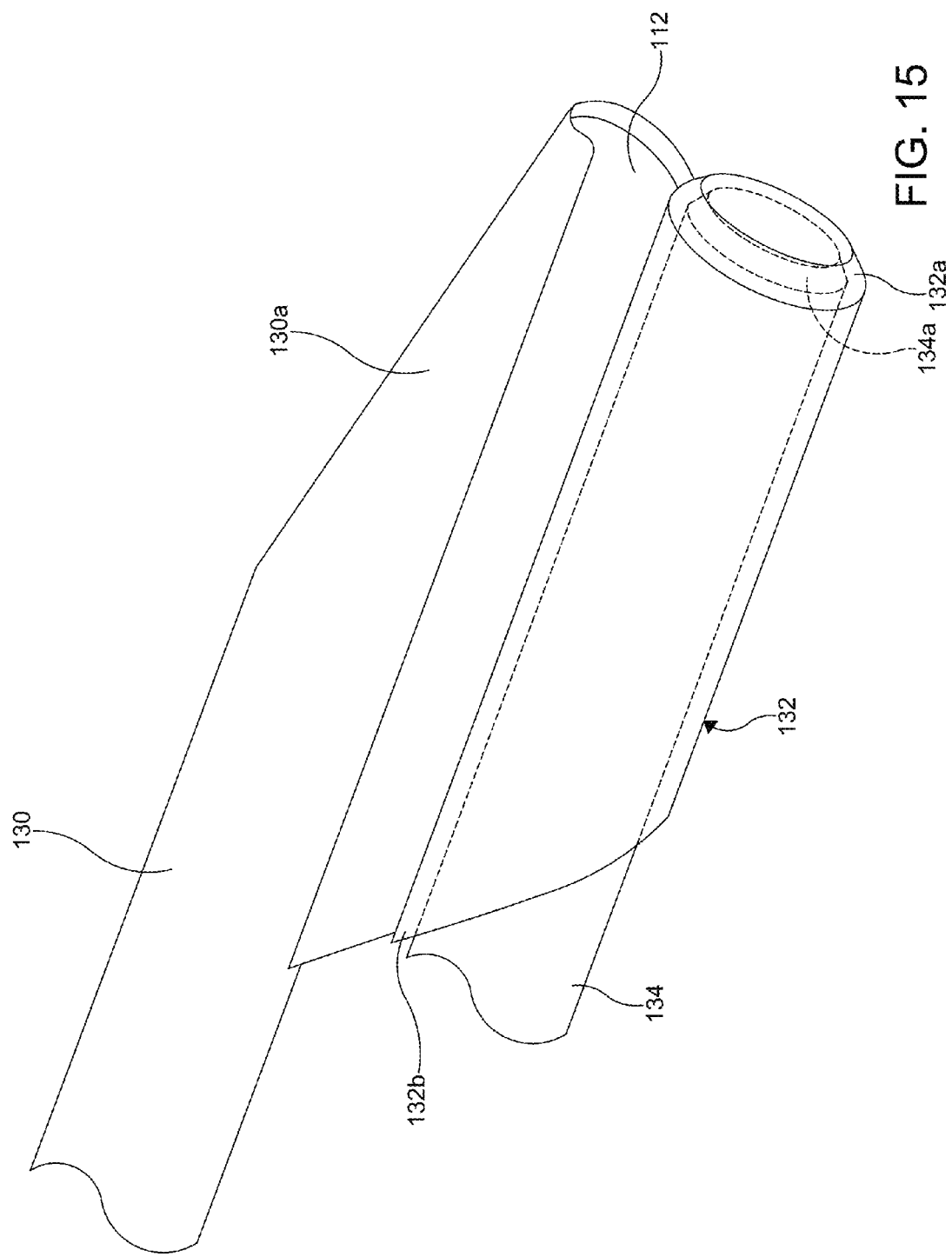
FIG. 15 is a plan view of a sixth embodiment of the intubation assembly rod illustrated in FIG. 8.

A sixth embodiment of the intubation assembly rod is shown at 130 in FIG. 15. The distal end 130a of the rod 130 is tapered or substantially cone-shaped and defines a leading end of the rod 130. The rod 130 includes a guide sleeve 132 having a first or distal end 132a, a second or proximal end 132b, and has a longitudinally extending substantially cylindrical channel 132c formed therethrough. The guide sleeve 132 is attached to the rod 130 by the substantially flat bridge 112 that extends between the rod 130 and the guide sleeve 132. The distal end 132a of the guide sleeve 132 has a frustoconical shape. The guide sleeve 132 is configured to retain a second embodiment of the flexible member, a portion of which is shown at 134. A distal end 134a of the flexible member 134 also has a frusto-conical shape, such that the distal end 134a of the flexible member 134 is retained within the distal end 132a of the guide sleeve 132. The rod 130 is otherwise substantially the same as the rod 102.

It will be understood that each embodiment of a rod and a guide sleeve described herein, including the rod 108 and the guide sleeve 110, the rod 116 and the guide sleeve 118, the rod 122 and the guide sleeve 124, and the rod 130 and the guide sleeve 132, may be formed without the substantially flat bridge 112. In such embodiments, the sleeves, 110, 118, 124, and 132 are mounted directly to the rods 108, 116, 122, and 130, respectively. The bridge 112 may have any width and length, and may be attached to the guide sleeves 110, 118, 124, and 132 at any point proximal to the distal ends of the guide sleeves 110,118,124, and 132, respectively.

Figure 19:
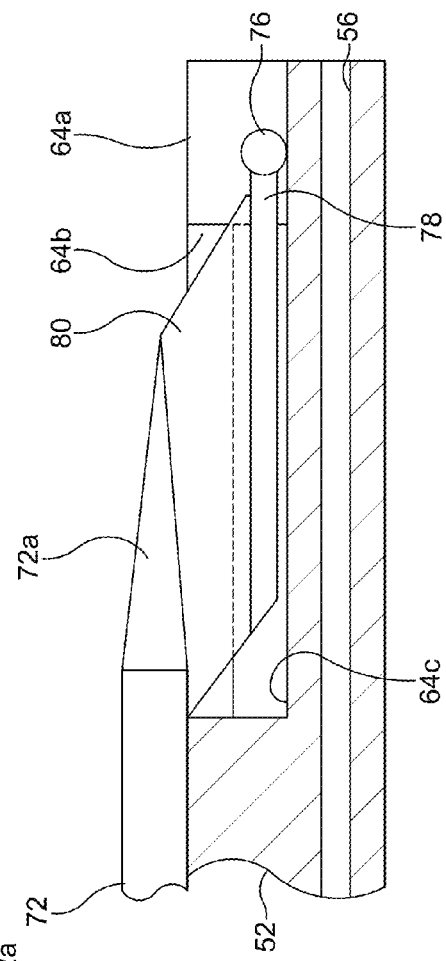
FIG. 19 is a cross-sectional view of a portion of the optical assembly illustrated in FIGS. 2 and 3 showing the intubation assembly rod mounted therein.

Prior to use, the guided introducer intubation assembly 38 is secured to the optical assembly 36 by inserting the guide member portion 78 of the guide rail 75 into the intubation assembly guide channel 64 via the first portion 64a until the guide member portion 78 is seated within the second portion 64c of the intubation assembly guide channel 64, the tip 76 is seated within the first portion 64a of the intubation assembly guide channel 64, and the bridge 80 extends through the second portion 64b of the intubation assembly guide channel 64, as shown in FIGS. 2 and 19. The flexible member 52 of the optical assembly 36 may be locked or fixedly positioned relative to the optical housing 50 by manually moving the mounting post 68b of the control device 68 into one of the notches 48.

Alternatively, a mechanical or electro-mechanical movement device (not shown) may be attached to the flexible member 52, between the flexible member 52 and the optical housing 50, or between the flexible member 52 and any desired portion of the endotracheal tube insertion device 30, and configured to selectively move the flexible member 52 longitudinally within the optical housing 50.

Prior to being inserted into the patient's airway, the guided introducer intubation assembly 38 and attached endotracheal tube 92 may be releasably attached to the endotracheal tube insertion device 30 within the attachment member 70, as best shown in FIG. 2.

In use, one operator or user may insert the blade assembly 34, with the attached optical assembly 36 and guided introducer intubation assembly 38, into the airway of a patient, until the distal end 35a of the blade body 35 is at the epiglottis. The distal end 52a of the flexible member 52 may then be moved outward of a distal end of the channel member 37 to gain a view of the vocal cords. The mounting post 68b of the control device 68 is moved out of the notch 48 within which it has been positioned, and the distal end 52a of the flexible member 52 may be moved outwardly in increments, such as about 0.5 cm increments, up to a distance of about 7 cm. As described above, the distal end 52a of the flexible member 52 may be moved relative to its axis A1 to gain a better view of the vocal cords, and may be locked or retained in a position selected by the user.

The user may then remove the endotracheal tube 92 from within the attachment member 70. Subsequently, the user may slide the guided introducer intubation assembly 38 forwardly into the trachea and outwardly of the guide channel 64 until the tip 76 is about 12 cm below or beyond the vocal cords, and the balloon cuff 96 is below the vocal cords. The balloon cuff 96 may then be inflated in a conventional manner. The blade assembly 34 and the optical assembly 36 may be removed from the patient. The guided introducer intubation assembly 38 may then be disconnected from the endotracheal tube 92 and also removed from the patient.

Advantageously, the improved endotracheal tube insertion device 30 includes the guided introducer intubation assembly 38, the optical assembly 36, and the blade assembly 34 that are interconnected and function as a single unit during endotracheal tube 92 positioning.

As a further advantage, the improved endotracheal tube insertion device 30 is a relatively simple tool that allows a user to gain and maintain full control of a patient or accident victim's airway without the experience of one who has performed hundreds or thousands of endotracheal intubation procedures. Users, such as first responders, without such significant experience may use the improved endotracheal tube insertion device 30 to intubate the airway of a patient with or without the assistance of a physician airway specialist who may be viewing remotely, but in real-time, the video of the procedure.

Advantageously, video of the airway may be transmitted via the internet in real time to a specialist anywhere in the world. This allows the specialist to provide advice and guidance to a less experienced or less knowledgeable user, whether the user and patient are in a hospital or at a remote accident site.

Although not illustrated, the optical assembly 36 may be formed with a longitudinally extending rail, similar to the guide member portion 78, and the guided introducer intubation assembly 38 may be formed with a corresponding longitudinally extending slot or groove within which the rail may be slidably mounted. A stop member, including but not limited to a retaining ball, such as similar to the spherical tip 76, may be provided on either a distal or proximal end of the rail or the groove to prevent proximal or rearward movement of the guided introducer intubation assembly 38 along the rail.

Figure 16:
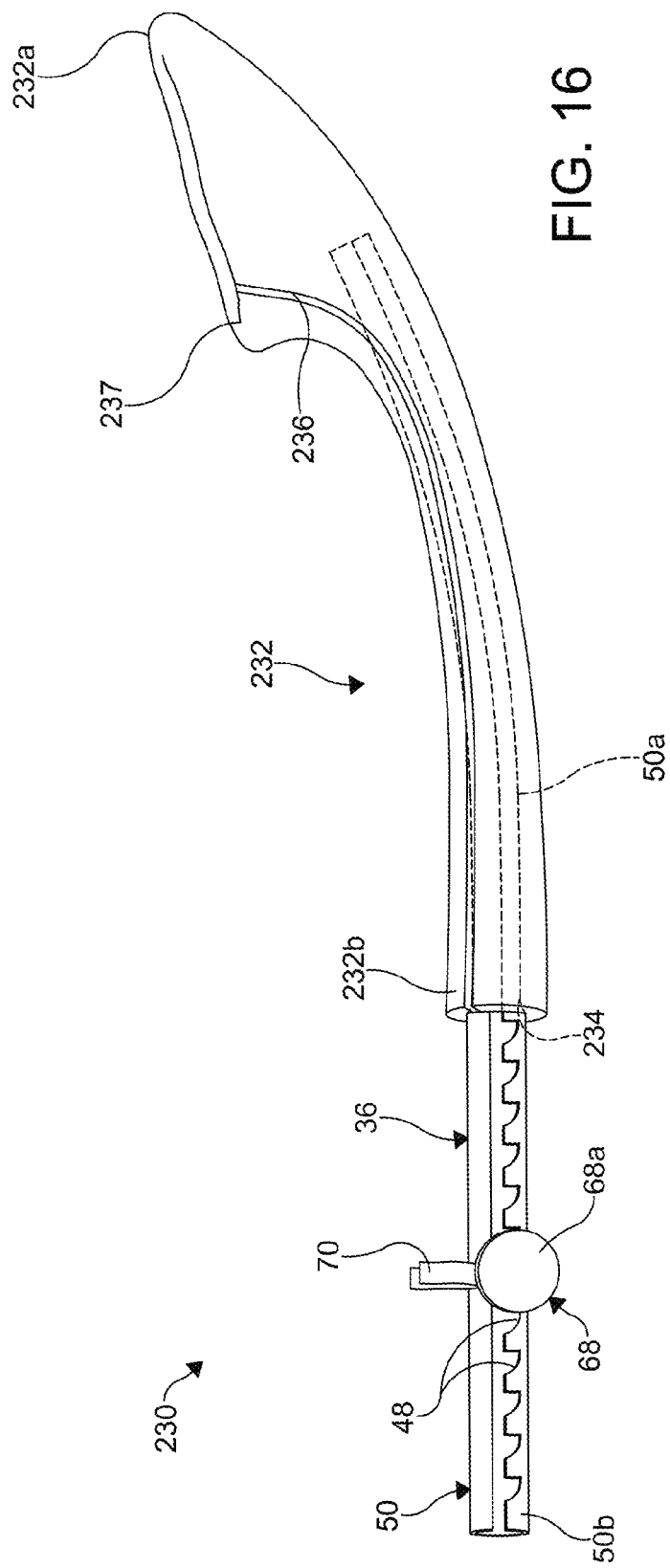
FIG. 16 is an elevational view of a portion of a second embodiment of an improved endotracheal tube insertion device in accordance with this invention.
Figure 17:
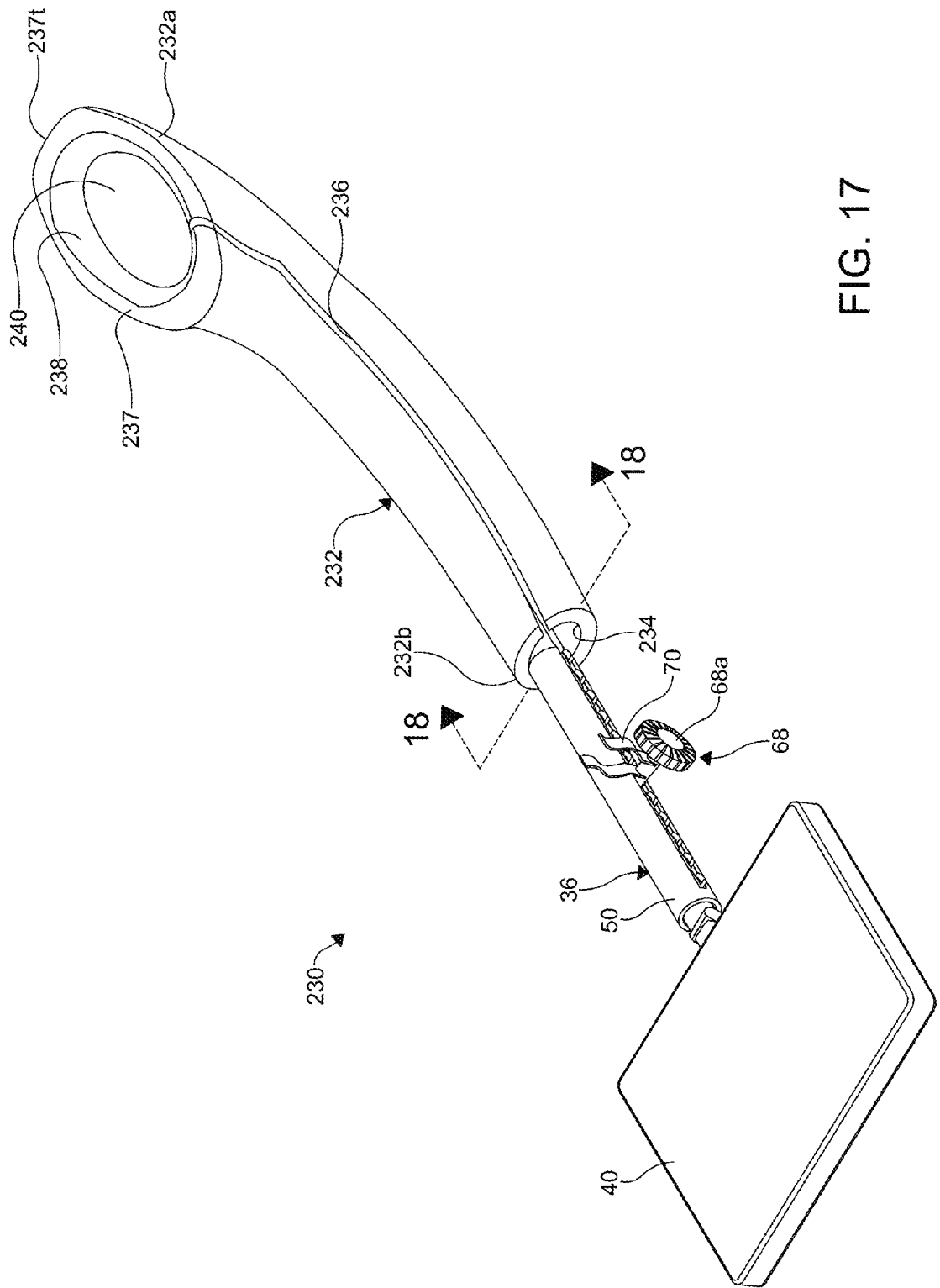
FIG. 17 is a perspective view of the second embodiment of the improved endotracheal tube insertion device illustrated in FIG. 16.
Figure 18:
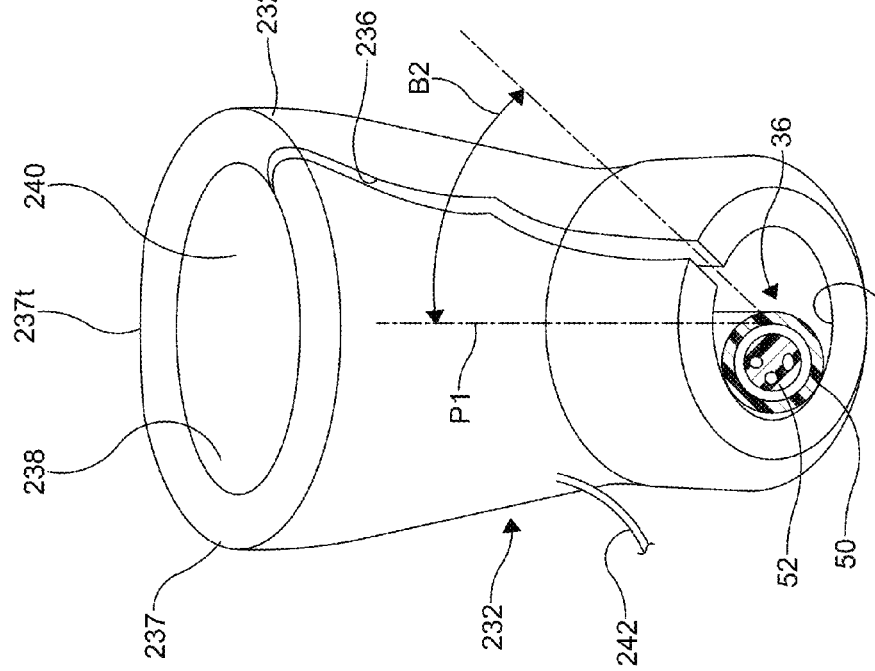
FIG. 18 is a cross-sectional view taken along the line 18-18 of FIG. 17.

A second embodiment of the endotracheal tube insertion device is shown at 230 in FIGS. 16 through 18. In FIG. 16, the endotracheal tube insertion device 230 is shown with the guided introducer intubation assembly 38 and the video monitor 40 removed for clarity. The endotracheal tube insertion device 230 also includes the optical assembly 36, described above.

Unlike the improved endotracheal tube insertion device 30, the improved endotracheal tube insertion device 230 does not include the blade assembly 34. If desired, the endotracheal tube insertion device 230 may include the handle 32. As shown in FIG. 16, the improved endotracheal tube insertion device 230 includes an insertion member configured as a supraglottic member 232 in lieu of the blade 35. The supraglottic member 232 includes a first or distal end 232a, a second or proximal end 232b, has a longitudinally extending passageway 234 formed therethrough, and a longitudinally extending slot 236 formed through a wall thereof. The slot 236 may have any desired length and width. In addition to the generally straight shape of the slot 236 shown, the slot 236 may have any other desired shape, such as a generally serpentine or wavy pattern (not shown) to assist in retaining the guided introducer intubation assembly 38 within the passageway 234.

The slot 236 facilitates removal of the guided introducer intubation assembly 38, as described below. In the illustrated embodiment, the passageway 234 has a substantially oval cross-sectional shape, as best shown in FIG. 18, providing space for the illustrated optical assembly 36 and the guided introducer intubation assembly 38, not shown in FIGS. 16 through 18. In the illustrated embodiment, the optical housing 50 of the optical assembly 36 is attached or mounted within the passageway 234. It will be understood that the optical housing 50 may be integrally formed with the supraglottic member 232, or attached by any desired means included with adhesive, by welding, or in a snap-fit arrangement to ensure that the optical housing 50 does not move relative to the supraglottic member 232 during use.

The guided introducer intubation assembly 38 is described as extending into and through the passageway 234 as best shown in FIGS. 17 and 18. Alternatively however, the passageway 234 may be configured large enough to only allow the optical assembly 36 to fit therein. In such an embodiment, the guided introducer intubation assembly 38 may be attached to the flexible member 52, but routed outside of the supraglottic member 232.

In the illustrated embodiment, and as best shown in FIG. 18, the longitudinally extending slot 236 is formed at an angle B2 from a plane P1 that vertically bisects the supraglottic member 232 (when viewing the cross-sectional view of the supraglottic member 232 in FIG. 18). In the illustrated embodiment, the angle B2 is within the range of about 30 degrees to about 60 degrees from the plane P1. Alternatively, the angle B2 may be any angle from 0 degrees to 360 degrees from the plane P1.

The supraglottic member 232 includes a generally bowl-shaped supraglottic cuff 237 formed at the distal end 232a thereof. The supraglottic cuff 237 may be conventional in the art and includes a cuff wall 238 and a cuff opening 240 into which the optical assembly 36 and the guided introducer intubation assembly 38 (not shown in FIGS. 16 through 18) extend. The illustrated passageway 234 has a substantially oval cross-sectional shape, however the passageway 234 may have any desired cross-sectional shape, such as substantially circular, and substantially rectangular. Additionally, the passageway 234 may have any other desired diameter or cross-sectional size.

The supraglottic cuff 237 may be a non-inflatable cuff, such as the I-gel® supraglottic airway manufactured by Intersurgical Ltd. The non-inflatable supraglottic cuff 237 may be formed of any gel-like or other substantially soft material designed to provide an anatomical, impression fit over the laryngeal inlet. Preferably, the shape, softness, and contours of the supraglottic cuff 237 accurately mirror the perilaryngeal anatomy. Alternatively, the supraglottic cuff 237, or any one or more portions thereof, may be inflatable and therefore include a conventional air inflation tube 242, such as shown in FIG. 18. The air inflation tube 242 may be attached to the supraglottic cuff 237 and configured for attachment to a source of air, such as a syringe. Although illustrated in one location, the air inflation tube 242 may be attached to the supraglottic cuff 237 at any desired location. It will be understood that the supraglottic cuff 237 may have any desired shape, including a shape configured to displace the epiglottis and laryngeal structures to optimize the user's view of the vocal cords. Advantageously, the inflatable supraglottic cuff 237 allows the user to more easily displace laryngeal structures such as the epiglottis.

In use, the improved endotracheal tube insertion device 230 differs from the improved endotracheal tube insertion device 30 in its position in the larynx for operation. For example, the improved endotracheal tube insertion device 230 is designed and configured to be inserted blindly into the mouth of a patient and advanced along the hard and soft palates until a distal tip cuff 237t of the supraglottic cuff 237 is seated in the hypopharynx with the cuff opening 240 facing the supraglottic structures. The flexible member 52 may then be advanced within the optical housing 50, carrying with it the guided introducer intubation assembly 38 in a manner similar to the method described above for use of the improved endotracheal tube insertion device 30 having the rigid blade body 35. Once the optical assembly 36 is optimally positioned and locked facing the vocal cords, the guided introducer intubation assembly 38 is advanced forward and off the optical assembly 36, as described above, such that the guided introducer intubation assembly 38 is positioned between the vocal cords and into the trachea.

The endotracheal tube 92 is positioned below the vocal cords and remains in the trachea. The flexible member 52, optical housing 50, and the supraglottic member 232 may then be removed together. Advantageously, the slot 236 in the supraglottic member 232 allows the supraglottic member 232, the flexible member 52, and the optical housing 50 to be removed from around the endotracheal tube 92, thus allowing the endotracheal tube 92 to remain in a desired position below the vocal cords. Finally, the guided introducer intubation assembly 38 may be removed from within the endotracheal tube 92.

Figure 20:
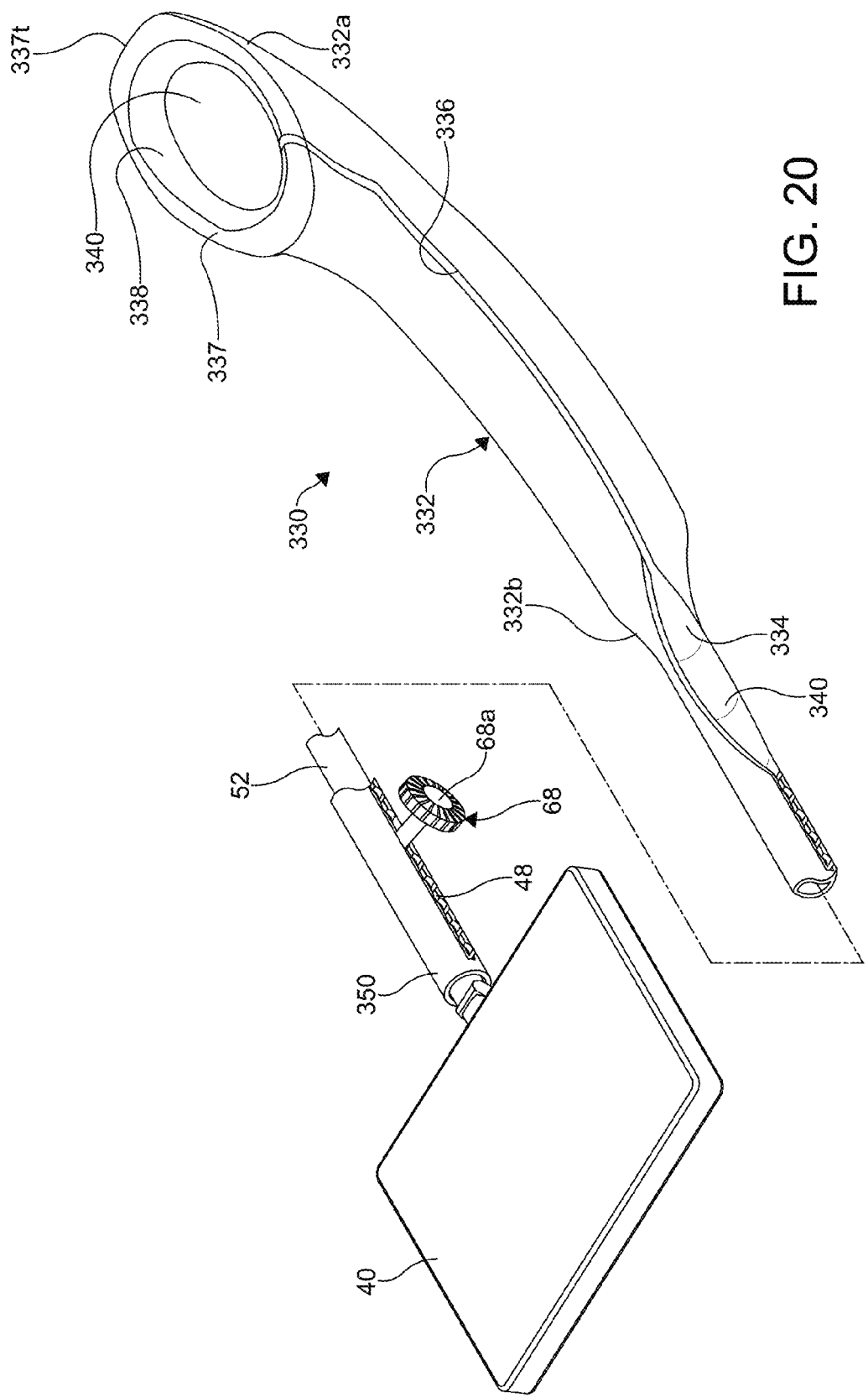
FIG. 20 is a perspective view of a third embodiment of the improved endotracheal tube insertion device in accordance with this invention.
Figure 21:
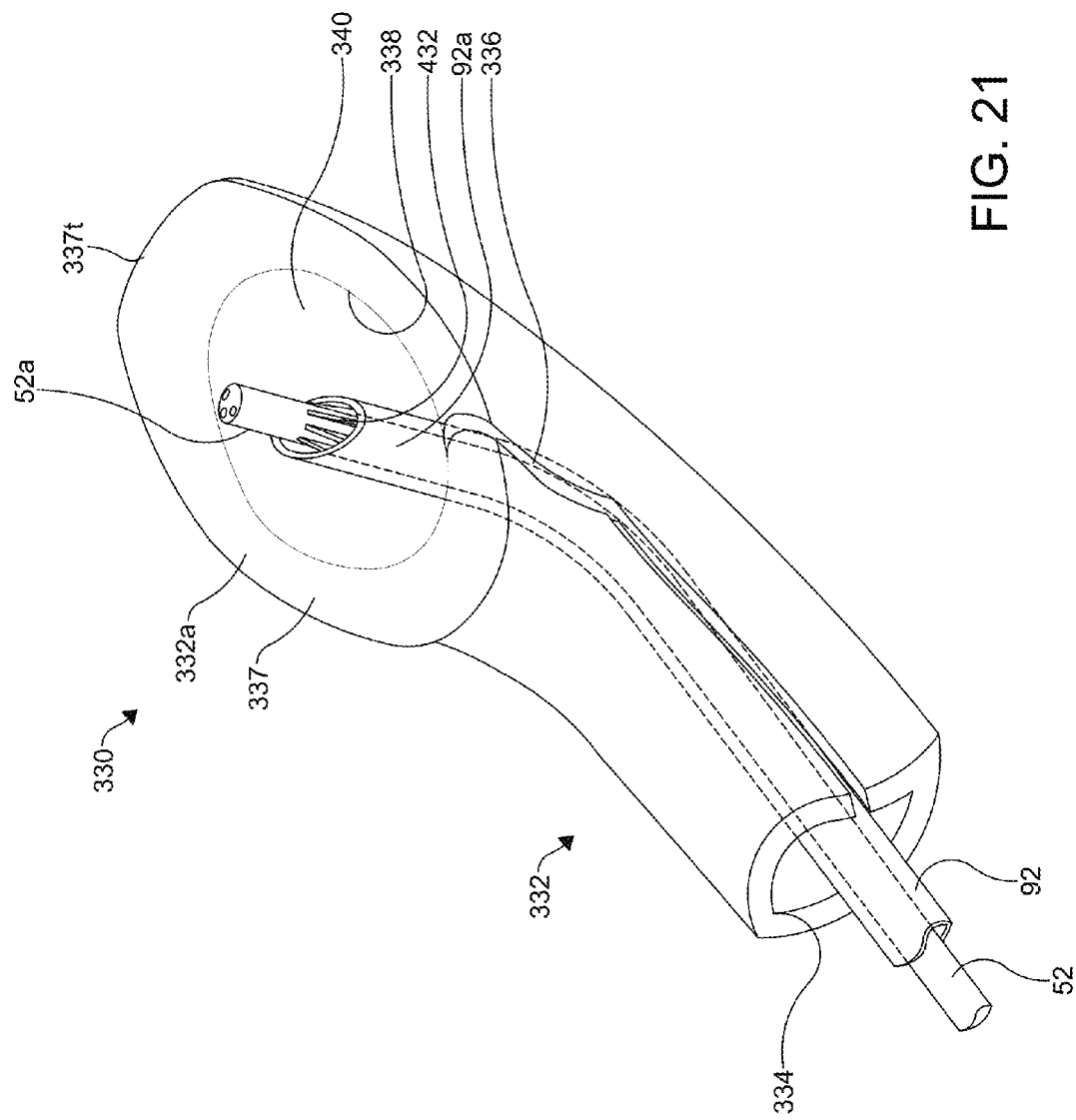
FIG. 21 is an enlarged perspective view of a portion of the third embodiment of the improved endotracheal tube insertion device illustrated in FIG. 20.

A third embodiment of the endotracheal tube insertion device is shown at 330 in FIGS. 20 and 21. The endotracheal tube insertion device 330 is similar to the endotracheal tube insertion device 230, includes the video monitor 40, and is configured to be used with the endotracheal tube 92 and the flexible member 52.

As shown in FIG. 20, the improved endotracheal tube insertion device 330 includes a supraglottic portion 332. The supraglottic portion 332 includes a first or distal end 332a, a second or proximal end 332b, has a longitudinally extending passageway 334 formed therethrough, and a longitudinally extending slot 336 formed through a wall thereof. Like the slot 236 described above, the slot 336 may have any desired length and width and may have any other desired shape, such as a generally serpentine or wavy pattern (not shown) to assist in retaining the endotracheal tube 92 within the passageway 334. The passageway 334 may have any desired shape, such as a substantially oval cross-sectional shape or a substantially cylindrical shape. It will be understood that the passageway 334 must be large enough to allow the endotracheal tube 92 to be inserted therein.

The supraglottic portion 332 includes a generally bowl-shaped supraglottic cuff 337 formed at the distal end 332a thereof. The supraglottic cuff 337 may be conventional in the art and includes a cuff wall 338 and a cuff opening 340 into which the concentrically arranged flexible member 52 and endotracheal tube 92 (best shown in FIG. 21) extend. Like the supraglottic cuff 237, the supraglottic portion 332 may include a non-inflatable supraglottic cuff 337, as described above. The supraglottic cuff 337, or any one or more portions thereof, may be inflatable, and thus may include the conventional air inflation tube 242 as shown in FIG. 18 and described above. The supraglottic cuff 337 may have any desired shape, including a shape configured to displace the epiglottis and laryngeal structures to optimize the user's view of the vocal cords. Advantageously, the inflatable supraglottic cuff 337 allows the user to more easily displace laryngeal structures such as the epiglottis.

An optical housing portion 350 extends outward of the proximal end 332b of the supraglottic portion 332. A large opening or sled area 340 is defined in the optical housing portion 350 adjacent the proximal end 332b of the supraglottic portion 332. The sled area 340 may be any desired size sufficient to allow the concentrically arranged flexible member 52 and endotracheal tube 92 to be inserted therein. The optical housing portion 350 may be attached to the supraglottic portion 332 by any desired means, such as with an adhesive, by a threaded connection, or by welding. Alternatively, the optical housing portion 350 may be integrally formed with the supraglottic portion 332, as shown in FIG. 20.

In the embodiment illustrated in FIG. 20, the flexible member 52 is inserted within the endotracheal tube 92. The endotracheal tube 92 with the flexible member 52 mounted therein is then inserted through the sled area 340 and into the passageway 334. The proximal end of the flexible member 52 may be secured within the optical housing portion 350 in the same manner that the flexible member 52 is secured within the second portion 50b of the optical housing 50, described above. The proximal end 92b of the endotracheal tube 92 and the attached connector 98 remain within the sled area 340, and may be releasably attached to the optical housing portion 350 or the flexible member 52.

As described above, the flexible member 52 and the concentrically mounted endotracheal tube 92 extend longitudinally through the passageway 334 of the supraglottic portion 332. In use, the endotracheal tube insertion device 330 may be inserted into the airway, and the flexible member 52 and the concentrically mounted endotracheal tube 92 may then be advanced below the vocal cords. Once the endotracheal tube 92 is positioned below the vocal cords, the flexible member 52 and the supraglottic portion 332 are removed. The flexible member 52 may be removed from the proximal end 92b of the endotracheal tube 92. The slot 336 in the supraglottic portion 332 allows the supraglottic portion 332 to be removed from around the endotracheal tube 92, thus allowing the endotracheal tube 92 to remain in a desired position below the vocal cords.

Referring to FIG. 21, the flexible member 52 and endotracheal tube 92 are shown within a portion of the supraglottic portion 332. As shown, the flexible member 52 and endotracheal tube 92 are concentrically arranged wherein the flexible member 52 is inserted within the endotracheal tube 92, and the endotracheal tube 92 is inserted into the passageway 334 as described above.

If desired, the distal end 52a of the flexible member 52 may have retention features such as ribs 432 having tapered leading edges similar to the ribs 74 on the rod 72, to retain the distal end 92a of the endotracheal tube 92 about the distal end 52a of the flexible member 52 during insertion into the airway. Alternatively, the distal end 52a of the flexible member 52 may have a frusto-conical shape, as shown in FIG. 15, thus also retaining the distal end 92a of the endotracheal tube 92 about the distal end 52a of the flexible member 52 during insertion into the airway. Additionally, the distal end 52a of the flexible member 52, in an area generally the same as the area in which the tapered leading edges of the ribs 432 shown in FIG. 21 are formed, may include an inflatable portion having a tapered or frusto-conical shaped leading edge.

Significantly, the ribs 432, particularly the shape and tapered leading edges of the ribs 432, or the alternative distal end 52a having the inflatable frusto-conical shaped portion, of the flexible member 52 of the improved endotracheal tube insertion device 330 are configured to prevent the leading edge or distal end 52a of the flexible member 52 from catching on laryngeal structures as the flexible member 52 and surrounding endotracheal tube 92 is advanced into the patient's airway, thus facilitating the delivery of the endotracheal tube 92 between the vocal cords and preventing trauma or injury to the vocal cords and other parts of the airway.

It will be understood that each of the improved endotracheal tube insertion devices 30, 230, and 330, illustrated and described herein, may be manufactured in any desired size. For example, the improved endotracheal tube insertion devices 30, 230, and 330 may be relatively small so as to be configured for use with pediatric patients, may be relatively large so as to be configured for use with adult patients.

The principle and mode of operation of this invention have been explained and illustrated in its preferred embodiment. However, it must be understood that this invention may be practiced otherwise than as specifically explained and illustrated without departing from its spirit or scope.

What is claimed is:

1. An intubation assembly for use in an endotracheal tube insertion device, the intubation assembly comprising:
    a rod having an elongated body having a first end and a second end;
    a guide system formed at the first end of the rod; and
    a connecting member mounted to the second end of the rod;
    wherein the first end of the rod is a distal end of the rod, and wherein the distal end of the rod is tapered.

2. The intubation assembly according to claim 1, wherein the rod includes a plurality of longitudinally and radially outwardly extending ribs, and wherein a distal end of each rib is tapered.

3. The intubation assembly according to claim 2, wherein the ribs have an arcuate cross-sectional shape and are radially compressible.

4. The intubation assembly according to claim 1, wherein the rod is configured to be relatively more flexible at its first end and relatively less flexible at its second end.

5. The intubation assembly according to claim 1, wherein a portion of the rod is inflatable.

6. The endotracheal tube insertion device according to claim 1, wherein the connecting member is longitudinally movable relative to the rod, the connecting member further configured for attachment to a connector of the endotracheal tube.

7. An endotracheal tube insertion device comprising:
    an insertion member;
    an optical assembly including an optical housing and an elongated flexible member disposed within the optical housing, the elongated flexible member having a first and a second end, the elongated flexible member movably mounted to the insertion member;
    an intubation assembly including an intubation assembly body and having a guide system formed thereon, the guide system configured for releasable attachment to the first end of the elongated flexible member of the optical assembly; and,
    an endotracheal tube carried by the intubation assembly body.

8. An endotracheal tube insertion device comprising:
    a supraglottic member including a first end, a second end, a longitudinally extending passageway formed therethrough, and a longitudinally extending slot formed through a wall thereof, and wherein the supraglottic member further includes a generally bowl-shaped supraglottic cuff formed at the first end thereof, the supraglottic cuff including a cuff wall and a cuff opening into which the optical assembly, the intubation assembly, and the endotracheal tube extend, the supraglottic cuff being further configured as one of an inflatable cuff, a partially inflatable cuff, and a non-inflatable cuff;
    an optical assembly movably mounted to the supraglottic member; and
    an intubation assembly including an intubation assembly rod having a guide system formed on the intubation assembly rod, the guide system configured for releasable attachment to the optical assembly.

9. The endotracheal tube insertion device according to claim 8, wherein the intubation assembly rod has an elongated body having a first end and a second end, and wherein the first end of the intubation assembly rod is tapered, the endotracheal tube insertion device further including:
    a guide system formed at the first end of the intubation assembly rod;
    a connecting member mounted to the second end of the intubation assembly rod; and
    an endotracheal tube carried by the intubation assembly.

10. The endotracheal tube insertion device according to claim 9, wherein the intubation assembly rod includes a plurality of longitudinally and radially outwardly extending ribs, wherein a distal end of each rib is tapered, and wherein the ribs have an arcuate cross-sectional shape and are radially compressible.

11. The endotracheal tube insertion device according to claim 9, wherein the optical assembly includes an optical housing and an elongated flexible member disposed within the optical housing, the elongated flexible member having a first and a second end, and wherein the flexible member includes an intubation assembly guide channel at the first end thereof, the intubation assembly guide channel configured to receive the guide system of the intubation assembly body.

12. The endotracheal tube insertion device according to claim 11, wherein the first end of the intubation assembly rod has a substantially cone-shaped surface defining a tapered leading end, and wherein the guide system includes a guide rail having an elongated guide member portion laterally retained in the intubation assembly guide channel in the flexible member.

13. The endotracheal tube insertion device according to claim 12, further including a substantially flat bridge that extends between the intubation assembly rod and the guide member portion and connects the guide member portion to the intubation assembly rod.

14. The endotracheal tube insertion device according to claim 11, wherein the first end of the intubation assembly rod has a substantially cone-shaped surface defining a tapered leading end, and wherein the guide system includes a guide sleeve mounted at the first end of the intubation assembly rod configured such that one of the optical housing and the elongated flexible member may be inserted through the guide sleeve.

15. The endotracheal tube insertion device according to claim 14, further including a substantially flat bridge that extends between the intubation assembly rod and the guide sleeve and connects the guide sleeve to the intubation assembly rod.

16. The endotracheal tube insertion device according to claim 7, wherein the flexible member includes an attachment member attached to the second end thereof, the attachment member configured to releasably retain the endotracheal tube and the intubation assembly body therein.

17. The endotracheal tube insertion device according to claim 16, further including a handle assembly; wherein the insertion member is a blade attached to the handle assembly, the blade having an elongated channel formed on a surface thereof, the channel configured to retain a portion of the optical assembly.

18. The endotracheal tube insertion device according to claim 16, wherein the flexible member includes an intubation assembly guide channel at the first end thereof, the intubation assembly guide channel configured to receive the guide system of the intubation assembly body.

19. The endotracheal tube insertion device according to claim 16, wherein the guide system is a first guide system and includes a channel, and the optical assembly includes a second guide system formed thereon, the second guide system configured for releasable attachment within the channel of the first guide system.

20. The endotracheal tube insertion device according to claim 16, wherein the intubation assembly body is a rod having a first end and a second end, and wherein the first end of the rod has a substantially cone-shaped surface defining a tapered leading end, and wherein the guide system includes a guide rail having an elongated guide member portion laterally retained in a channel formed in the optical assembly.

21. The endotracheal tube insertion device according to claim 20, further including a substantially flat bridge that extends between the rod and the guide member portion and connects the guide member portion to the rod.

22. The endotracheal tube insertion device according to claim 21, wherein the guide member portion includes a substantially spherical tip formed at a distal end thereof.

23. The endotracheal tube insertion device according to claim 17, wherein the intubation assembly body is a rod having a first end and a second end, wherein the first end of the rod has a substantially cone-shaped surface defining a tapered leading end, wherein the guide system includes a guide sleeve mounted at the first end of the rod configured such that the optical assembly may be inserted through the guide sleeve, and such that the guide sleeve can be slidably mounted within the channel of the blade.

24. The endotracheal tube insertion device according to claim 23, further including a substantially flat bridge that extends between the rod and the guide sleeve and connects the guide sleeve to the rod.

25. The endotracheal tube insertion device according to claim 23, wherein a leading edge of the guide sleeve is tapered.

26. The endotracheal tube insertion device according to claim 16, wherein the insertion member is a supraglottic member, the supraglottic member including a first end, a second end, a longitudinally extending passageway formed therethrough, and a longitudinally extending slot formed through a wall thereof, and wherein the supraglottic member further includes a generally bowl-shaped supraglottic cuff formed at the first end thereof, the supraglottic cuff including a cuff wall and a cuff opening into which the optical assembly and the intubation assembly extend, the supraglottic cuff being further configured as one of an inflatable cuff, a partially inflatable cuff, and a non-inflatable cuff.

27. An endotracheal tube insertion device comprising:
a supraglottic member including a first end, a second end, a longitudinally extending passageway formed therethrough, and a longitudinally extending slot formed through a wall thereof, and wherein the supraglottic member further includes a generally bowl-shaped supraglottic cuff formed at the first end thereof, the supraglottic cuff including a cuff wall and a cuff opening into which the optical assembly and the endotracheal tube extend, the supraglottic cuff being further configured as one of an inflatable cuff, a partially inflatable cuff, and a non-inflatable cuff;
an optical assembly movably mounted to the supraglottic member; and
an endotracheal tube carried by the optical assembly.

* * * * *